(12) United States Patent
Wulfert

(10) Patent No.: US 8,148,355 B2
(45) Date of Patent: Apr. 3, 2012

(54) PHOPHYLACTIC AND THERAPEUTIC USE OF HYDROXYSTEROIDS

(75) Inventor: Ernst Wulfert, Brussels (BE)

(73) Assignee: Hunter-Fleming Limited, Bristol (GB)

( * ) Notice: Subject to any disclaimer, the term of this patent is extended or adjusted under 35 U.S.C. 154(b) by 1307 days.

(21) Appl. No.: 10/486,499

(22) PCT Filed: Aug. 13, 2002

(86) PCT No.: PCT/GB02/03770
§ 371 (c)(1),
(2), (4) Date: Jul. 8, 2004

(87) PCT Pub. No.: WO03/015791
PCT Pub. Date: Feb. 27, 2003

(65) Prior Publication Data
US 2004/0248868 A1    Dec. 9, 2004

(30) Foreign Application Priority Data

Aug. 14, 2001 (GB) .................................. 0119810.0

(51) Int. Cl.
*A61K 31/56* (2006.01)
*A61K 38/22* (2006.01)
*A61K 38/36* (2006.01)
*A61K 38/00* (2006.01)
*C07K 14/575* (2006.01)
*A61P 9/00* (2006.01)

(52) U.S. Cl. ....... 514/182; 514/9.7; 514/14.9; 514/15.4; 514/16.4

(58) Field of Classification Search .......................... None
See application file for complete search history.

(56) References Cited

U.S. PATENT DOCUMENTS 5,686,438 A * 11/1997 Daynes et al. ................. 514/178
5,753,640 A    5/1998 Araneo et al.
5,792,759 A    8/1998 Quadri et al.
6,187,767 B1 *  2/2001 Araneo et al. ................. 514/178
7,718,639 B2 *  5/2010 Wulfert et al. ................. 514/178
2003/0186953 A1 * 10/2003 Wulfert et al. ................. 514/178

FOREIGN PATENT DOCUMENTS

| WO | WO 96 40152 | 12/1996 |
| WO | WO/98/55074 | 10/1998 |
| WO | WO 98/55074 | * 12/1998 |
| WO | WO/9911271 | 3/1999 |
| WO | WO 99/52532 | * 4/1999 |
| WO | WO 99 52532 | 10/1999 |
| WO | WO 01 60375 | 8/2001 |
| WO | WO 02 00224 | 1/2002 |
| WO | WO/02/00225 | 3/2002 |

OTHER PUBLICATIONS

U.S. Appl. No. 12/639,708, filed Dec. 2009, Wulfert et al.*
Rosen Ken et al. Neurosteroid Hydroxylase Cyp7b Vivid reporter acttivity in denate gyrus of Gene-targeted mice and abolition of a widespread pathway of steroid and oxysterol hydroxylation Journal of Biological Chemistry vol. 276 No. 26-29 Jun. 2001 p. 23943, 23944 and 23938.
Jarrar D, et al. "Dhea: a novel adjunct for the treatment of male trauma patients" Trends in Molecular Medicine, vol. 7, No. 2, Feb. 2001 pp. 81-85.
Belokov, et al Course for Student of Higher School Pharmaceutical Chemistry 1993 vol. 1 43-47.
Rosen Ken at al. Neurosteroid Hydroxylase Cyp7b. Vivid reporter acttivity in denate gyrus of Gene-targeted mice and abolition of a widespread pathway of steroid and oxysterol hydroxylation Journal of Biological Chemistry vol. 276 No. 26-29 Jun. 2001 p. 23943, 23944 and 23938.
Jarrar D, at al. "Dhea: a novel adjunct for the treatment of male trauma patients" Trends in Molecular Medicine, vol. 7, No. 2, Feb. 2001 pp. 81-85.

* cited by examiner

*Primary Examiner* — Johann Richter
*Assistant Examiner* — Mei-Ping Chui
(74) *Attorney, Agent, or Firm* — Pearl Cohen Zedek Latzer, LLP

(57) ABSTRACT

3-Hydroxy-7-hydroxy steroids and 3-oxo-7-hydroxy steroids, especially the 7β-isomers thereof, and pharmaceutically acceptable esters thereof are useful for protection against ischaemia-induced damage to peripheral organs, such as the heart or kidneys, as well as treatment of spiral cord injury.

5 Claims, 6 Drawing Sheets

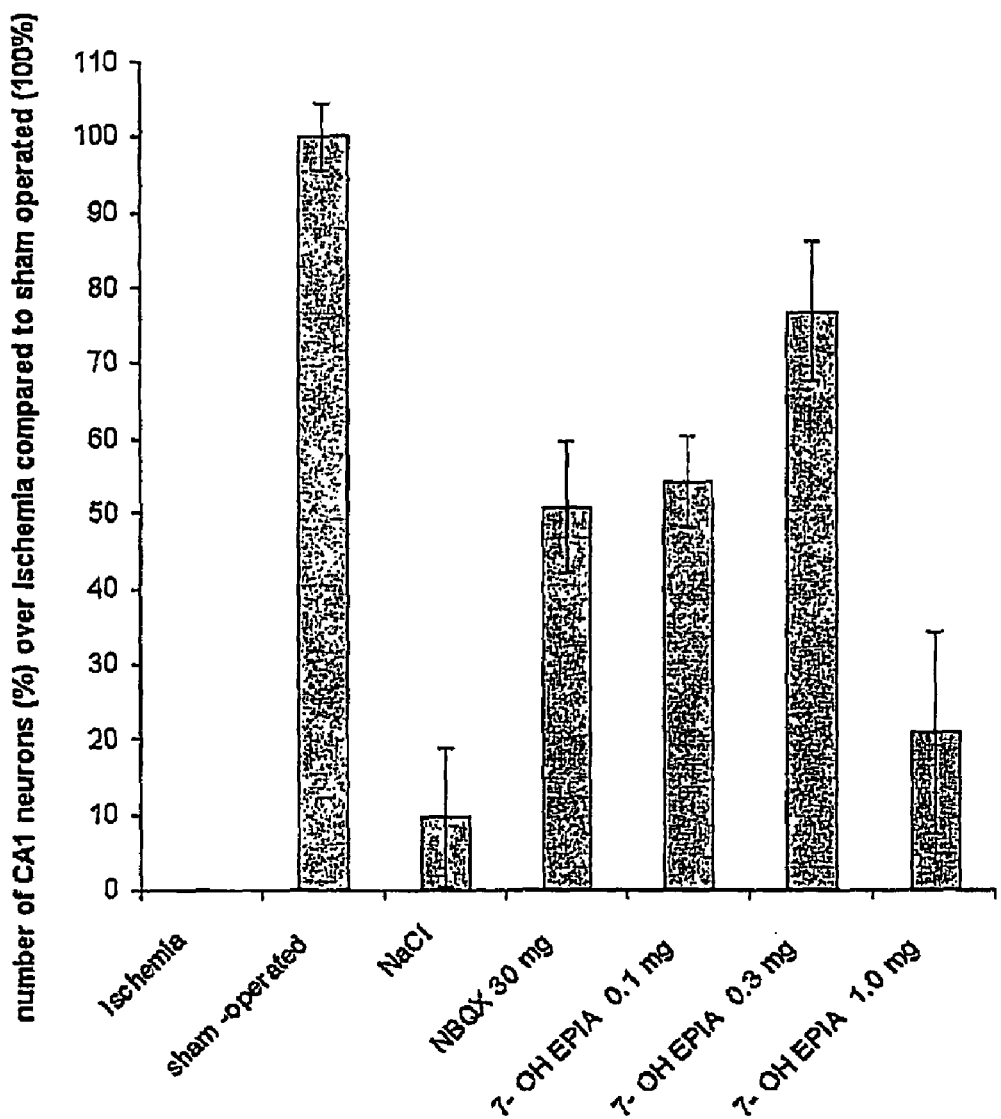

PHOPHYLACTIC AND THERAPEUTIC USE OF HYDROXYSTEROIDS

CROSS-REFERENCE TO RELATED APPLICATIONS

This application is a National Phase Application of PCT International Application No. PCT/GB02/03770, International Filing Date Aug. 13, 2002, claiming priority of Great Britain Patent Application, GB 0119810.0, filed Aug. 14, 2001.

The present invention relates to certain new prophylactic and therapeutic uses of 3-hydroxy-7-hydroxy-steroid compounds and of certain ketone derivatives thereof, and specifically to the use of these compounds for the prevention or treatment of damage caused by ischaemic stress of peripheral organs, such as the heart or the kidneys, as well as treatment of spinal cord injury.

Using a specific model for neuroprotection, we have demonstrated that compounds of this type have neuroprotective activity. We have now discovered that the same mode of action that results in this neuroprotective effect also operates in the tissues of peripheral organs, such as the heart and kidneys, and so the compounds have a cardioprotective effect and the ability to protect against ischaemic renal damage also.

Thus, the present invention provides the use of a 3-hydroxy-7-hydroxy steroid or a 3-oxo-7-hydroxy steroid or a pharmaceutically acceptable ester thereof for the manufacture of a medicament for protection against ischaemic damage to tissues of peripheral organs (i.e. any functional tissue in the body except the brain and the spinal cord), especially cardiac or renal damage, and for the treatment of spinal cord injury-induced damage to the spinal cord.

A particular class of compounds which are preferred for use in the present invention are the 7β-hydroxy steroids, and, of these, the compounds which are of especial interest to the present invention are the 3β,7β-dihydroxy steroids and pharmaceutically acceptable esters thereof.

Preferred esters are carboxylic acid and amino acid esters.

Examples of optionally substituted 3β,7β-dihydroxy steroids and pharmaceutically acceptable esters and other derivatives thereof which may be used in the present invention are those compounds of formula (I):

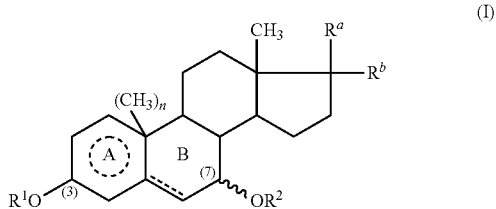

wherein
$R^1$ and $R^2$ are the same as or different from each other and each represents a hydrogen atom, an alkyl group having from 1 to 6 carbon atoms, an alkenyl group having from 2 to 6 carbon atoms, an alkynyl group having from 2 to 6 carbon atoms, an aryl group having from 6 to 10 carbon atoms, a formyl group, an alkylcarbonyl group having from 2 to 7 carbon atoms, an alkenylcarbonyl group having from 3 to 7 carbon atoms, an alkynylcarbonyl group having from 3 to 7 carbon atoms, an arylcarbonyl group having from 7 to 11 carbon atoms, an aralkylcarbonyl group having from 8 to 15 carbon atoms, an aralkenylcarbonyl group having from 9 to 15 carbon atoms, a residue of an amino acid, or a heterocyclic-carbonyl group, as defined below;
one of $R^a$ and $R^b$ represents a group of formula —$R^c$, preferably in the β configuration, and the other represents a hydrogen atom, or $R^a$ and $R^b$ together represent an oxo group;
$R^c$ represents an alkanoyl group having from 1 to 6 carbon atoms, an aryl-carbonyl group, in which the aryl part is an aromatic carbocyclic group having from 6 to 10 ring carbon atoms, a heterocyclic-carbonyl group, as defined below, or a group of formula —$OR^4$, where $R^4$ represents any one of the groups and atoms defined above for $R^1$ and $R^2$;
the ring A,

is a benzene or cyclohexane ring;
when ring A is a cyclohexane ring, the dotted line in ring B represents a single or double carbon-carbon bond, and n is 1; or when ring A is a benzene ring, the dotted line in ring B represents a single carbon-carbon bond and n is 0;
said heterocyclic-carbonyl group is a group of formula $R^3$—CO, where $R^3$ represents a heterocyclic group having from 3 to 7 ring atoms, of which from 1 to 3 are hetero-atoms selected from nitrogen atoms, oxygen atoms and sulphur atoms, and the remaining atom or atoms of which there is at least one is or are carbon atoms;
said alkyl, alkenyl and alkynyl groups and the alkyl, alkenyl and alkynyl parts of said arylcarbonyl, alkenylcarbonyl and alkynylcarbonyl groups being unsubstituted or having at least one of the following substituents ψ:
substituents ψ: hydroxy groups, mercapto groups, halogen atoms, amino groups, allylamino groups having from 1 to 6 carbon atoms, dialkylamino groups in which each alkyl group has from 1 to 6 carbon atoms, carbamoyl groups, nitro groups, alkoxy groups having from 1 to 6 carbon atoms, alkylthio groups having from 1 to 6 carbon atoms, carboxy groups, alkoxycarbonyl groups and unsubstituted aryl groups having from 6 to 10 carbon atoms;
said aryl groups, said heterocyclic groups, and the aryl parts of said arylcarbonyl groups and said aralkylcarbonyl groups being substituted or having at least one of the following substituents ξ;
substituents ξ: any of substituents ψ, and alkyl groups having from 1 to 6 carbon atoms, hydroxyalkyl groups having from 1 to 6 carbon atoms, and haloalkyl groups having from 1 to 6 carbon atoms;
and pharmaceutically acceptable salts and esters thereof.

The activity of the compounds of the present invention is illustrated by the accompanying drawings, in which:

FIG. 1C shows data of Example 22 presented as absolute percentage of neuroprotection when the number of surviving neurons in the ischaemia group was set to zero and those of the sham operated group was set to 100%;

Figure 5:
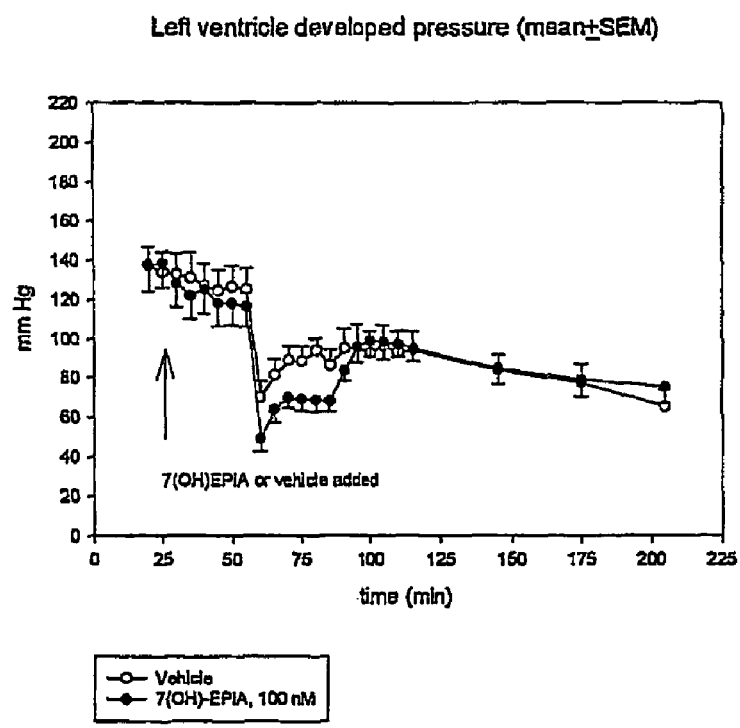
Figure 6:
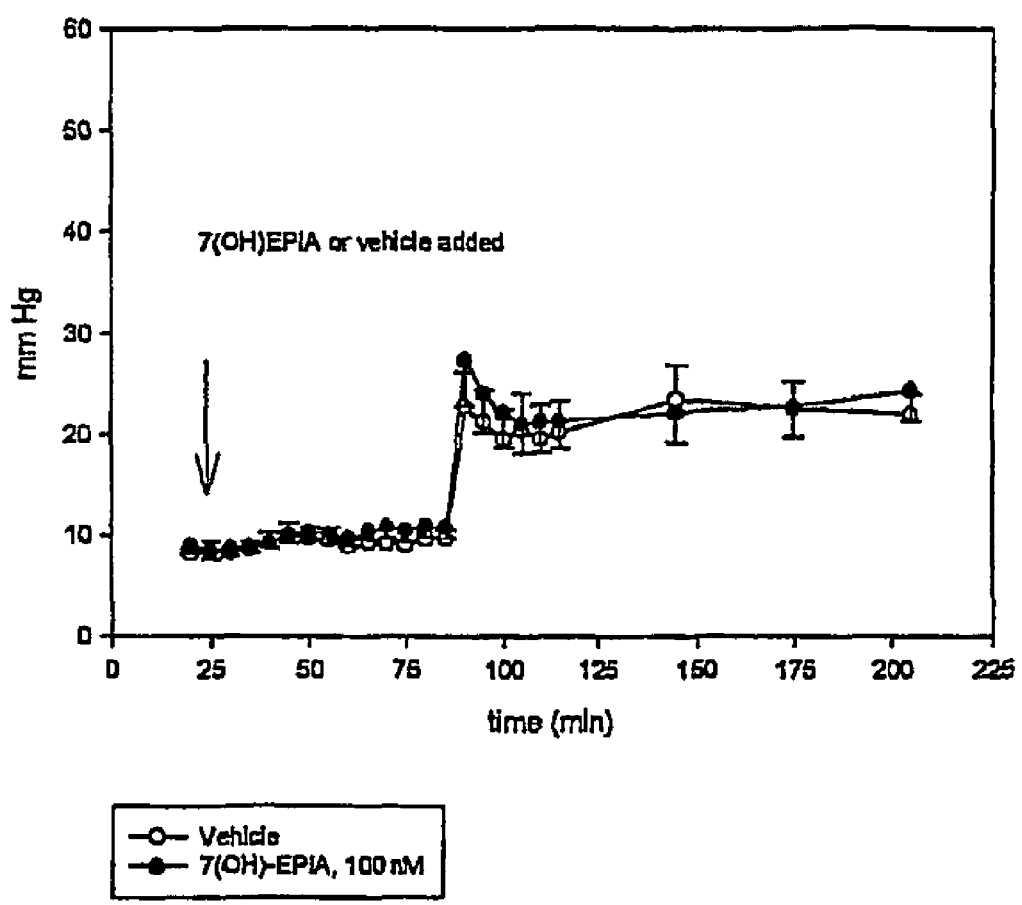

FIG. 5 shows the left ventricular developed pressure in Example 23 in control vehicle treated hearts and 7β-OH EPIA treated hearts before, during and after regional ischaemia; 7β-OH EPIA was added to the perfusate at 25 minutes, regional ischaemia was introduced at 55 minutes, the ischaemic area was reperfused at 85 minutes; and FIG. 6 shows the end diastolic pressure in Example 23 in control vehicle treated hearts and 7β-OH EPIA treated hearts before, during and after regional ischaemia; 7β-OH EPIA was added to the perfusate at 25 minutes, regional ischaemia was introduced at 55 minutes, the ischaemic area was reperfused at 85 minutes.

In the above compounds of formula (I), the group —$OR^2$ at the 7-position may be in the α or β configuration, but is preferably in the β configuration.

More preferably, in the compounds of formula (I):

$R^1$ and $R^2$ are the same as or different from each other and each represents a hydrogen atom, an alkyl group having from 1 to 6 carbon atoms, an optionally substituted phenyl group, a formyl group, an alkylcarbonyl group having from 2 to 5 carbon atoms, an arylcarbonyl group having from 7 to 11 carbon atoms, an aralkylcarbonyl group having from 8 to 15 carbon atoms, a residue of an amino acid, or a heterocyclic-carbonyl group, as defined below; we particularly prefer that $R^1$ and $R^2$ should both represent hydrogen atoms;

one of $R^a$ and $R^b$ represents an alkanoyl group having from 1 to 6 carbon atoms or a group of formula —$OR^4$, where $R^4$ represents any one of the groups and atoms defined above for $R^1$ and $R^2$, preferably in the β configuration, and the other represents a hydrogen atom, or $R^a$ and $R^b$ together represent an oxo group; we particularly prefer that $R^a$ and $R^b$ should together represent an oxo group, or that one of $R^a$ and $R^b$ should represent a hydrogen atom and the other should represent a hydroxy group or an alkanoyl group having from 1 to 4 carbon atoms, especially a hydroxy group or an acetyl group;

said heterocyclic-carbonyl group is a group of formula $R^3$—CO, where $R^3$ represents a heterocyclic group having from 3 to 7 ring atoms, of which from 1 to 3 are hetero-atoms selected from nitrogen atoms, oxygen atoms and sulphur atoms, and the remaining atom or atoms of which there is at least one is or are carbon atoms.

Most preferred compounds of formula (I) are those compounds in which:

$R^1$ and $R^2$ both represent hydrogen atoms; and $R^a$ and $R^b$ together represent an oxo group, or one of $R^a$ and $R^b$ represents a hydrogen atom and the other represents a hydroxy group or an alkanoyl group having from 1 to 4 carbon atoms, especially a hydroxy group or an acetyl group;

and pharmaceutically acceptable esters thereof.

Examples of 3-oxo-7β-hydroxy steroids which may be used in the present invention are those compounds of formula (II):

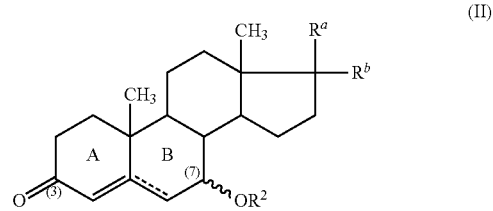

in which $R^a$, $R^b$ and $R^2$ are as defined above, and preferably $R^a$ and $R^b$ together represent an oxo group, or one of $R^a$ and $R^b$ represents a hydrogen atom and the other represents a hydroxy group, preferably in the β-configuration, or an acetyl group;

and pharmaceutically acceptable esters thereof.

In the above compounds of formula (II), the group —$OR^2$ at the 7-position may be in the α or β configuration, but is preferably in the β configuration.

More preferably, in the compounds of formula (II):

$R^2$ represents a hydrogen atom, an alkyl group having from 1 to 6 carbon atoms, an optionally substituted phenyl group, a formyl group, an alkylcarbonyl group having from 2 to 5 carbon atoms, an arylcarbonyl group having from 7 to 11 carbon atoms, an aralkylcarbonyl group having from 8 to 15 carbon atoms, or a heterocyclic-carbonyl group, as defined below; we particularly prefer that $R^2$ should represent a hydrogen atom;

one of $R^a$ and $R^b$ represents an alkanoyl group having from 1 to 6 carbon atoms or a group of formula —$OR^4$, where $R^4$ represents any one of the groups and atoms defined above for $R^2$, preferably in the β configuration, and the other represents a hydrogen atom, or $R^a$ and $R^b$ together represent an oxo group; we particularly prefer that $R^a$ and $R^b$ should together represent an oxo group, or that one of $R^a$ and $R^b$ should represent a hydrogen atom and the other should represent a hydroxy group or an alkanoyl group having from 1 to 4 carbon atoms, especially a hydroxy group or an acetyl group;

said heterocyclic-carbonyl group is a group of formula $R^3$—CO, where $R^3$ represents a heterocyclic group having from 3 to 7 ring atoms, of which from 1 to 3 are hetero-atoms selected from nitrogen atoms, oxygen atoms and sulphur atoms, and the remaining atom or atoms of which there is at least one is or are carbon atoms;

and pharmaceutically acceptable esters thereof.

Most preferred compounds of formula (II) are those compounds in which:

$R^2$ represents a hydrogen atom; and $R^a$ and $R^b$ together represent an oxo group, or one of $R^a$ and $R^b$ represents a hydrogen atom and the other represents a hydroxy group or an alkanoyl group having from 1 to 4 carbon atoms, especially a hydroxy group or an acetyl group;

and pharmaceutically acceptable esters thereof.

In the compounds of the present invention, where $R^1$, $R^2$, $R^4$ or substituent is an alkyl group, this may be a straight or branched chain alkyl group having from 1 to 6 carbon atoms, and examples include the methyl, ethyl, propyl, isopropyl, butyl, isobutyl, sec-butyl, t-butyl, pentyl, 1-methylbutyl, 2-methylbutyl, 3-methylbutyl, 1-ethylpropyl, 2-ethylpropyl, 1,1-dimethylpropyl, hexyl, 1-methylpentyl, 2-methyl-pentyl, 3-methylpentyl, 4-methylpentyl, 1-ethylbutyl, 2-ethylbutyl, 3-ethylbutyl, t-hexyl, and 1,1-dimethylpentyl groups, of which those groups having from 1 to 4 carbon atoms are preferred, the methyl and ethyl groups being most preferred.

Where $R^1$, $R^2$ or $R^4$ represents an alkenyl group, this may be a straight or branched chain alkenyl group having from 2 to 6 carbon atoms, and examples include the vinyl, 1-propenyl, allyl, isopropenyl, methallyl, 1-, 2-, 3-butenyl, isobutenyl, 1-, 2-, 3-, 4-pentenyl and 1-, 2-, 3-, 4-, 5-hexenyl groups, of which those alkenyl groups having from 2 to 4 carbon atoms are preferred, the vinyl and allyl groups being most preferred.

Where $R^1$, $R^2$ or $R^4$ represents an alkynyl group, this may be a straight or branched chain alkynyl group having from 2 to 6 carbon atoms, and examples include the ethynyl, 1-, 2-propynyl, 1-, 2-, 3-butynyl, isobutynyl, 1-, 2-, 3-, 4-pentynyl and 1-, 2-, 3-, 4-, 5-hexynyl groups, of which those alkynyl groups having from 2 to 4 carbon atoms are preferred.

Where $R^1$, $R^2$, $R^4$ or substituent $\psi$ represents an aryl group, this is an aromatic carbocyclic group having from 6 to 10 carbon atoms. Examples of such groups include the phenyl, 1-naphthyl, 2-naphthyl and indenyl groups, of which the phenyl group is preferred. Except in the case of substituent $\psi$, these groups may be substituted or unsubstituted. Where the group is substituted, the number of substituents is limited only by the number of substitutable positions, and possibly, in some instances, by steric constraints. Thus, in the case of the phenyl groups, the maximum number of substituents is 5, in the case of the naphthyl groups, the maximum number of substituents is 7 and so on. However, a preferred number of substituents is from 1 to 3, and the substituents are as hereafter described.

Where $R^1$, $R^2$ or $R^4$ represents an alkylcarbonyl group, this is an alkanoyl group, which may be a straight or branched chain group having from 2 to 7 carbon atoms (i.e. from 1 to 6 carbon atoms in the alkyl part), and examples include the acetyl, propionyl, butyryl, isobutyryl, valeryl, isovaleryl, pivaloyl, hexanoyl, and heptanoyl groups, of which those groups having from 2 to 5 carbon atoms are preferred, the acetyl and propionyl groups being most preferred. The alkyl portion of this group may be substituted or unsubstituted, and, if substituted, the substituents are selected from substituents $\psi$. Examples of such substituted groups include the alanyl, β-alanyl, phenylalanyl, asparaginyl, cysteinyl, glycoloyl, glycyl, methionyl, ornithyl, glyceroyl, tropoyl, glutaminyl, glutamyl, homocysteinyl, seryl, homoseryl, threonyl, lactoyl, leucyl, isoleucyl, norleucyl, lysyl, valyl, norvalyl and sarcosyl groups.

Where $R^1$, $R^2$ or $R^4$ represents an alkenylcarbonyl group, this may be a straight or branched chain alkenylcarbonyl group having from 3 to 7 carbon atoms, and examples include the acryloyl, methacryloyl, crotonoyl, isocrotonoyl, 3-butenoyl, pentenoyl and hexenoyl groups, of which those alkenylcarbonyl groups having from 3 to 5 carbon atoms are preferred, the acryloyl and methacryloyl groups being most preferred.

Where $R^1$, $R^2$ or $R^4$ represents an alkynylcarbonyl group, this may be a straight or branched chain alkynylcarbonyl group having from 3 to 7 carbon atoms, and examples include the propioloyl, 3-butynylcarbonyl, pentynylcarbonyl and hexynylcarbonyl groups, of which those alkynylcarbonyl groups having from 3 to 5 carbon atoms are preferred.

Where $R^c$, $R^1$, $R^2$ or $R^4$ represents an arylcarbonyl group, the aryl part of this may be any of the aryl groups defined and exemplified above. Preferred arylcarbonyl groups include the benzoyl, o-, m- or p-toluoyl, o-, m- or p-anisoyl, o-, m- or p-hydroxybenzoyl, picryl, galloyl, protocatechuoyl, vaniloyl, veratroyl, anthraniloyl, 1-naphthoyl and 2-naphthoyl groups.

Where $R^1$, $R^2$ or $R^4$ represents an aralkylcarbonyl or aralkenylcarbonyl group, the aryl and, as the case may be, alkyl or alkenyl group may be any of those groups defined and exemplified above. Specific examples of such groups include the phenylacetyl, 3-phenylpropionyl, benziloyl, tyrosyl, atropoyl, hydratropoyl and cinnamoyl groups.

Where $R^c$, $R^1$, $R^2$ or $R^4$ represents a heterocyclic-carbonyl group, this is a group of formula $R^3$—CO—, where $R^3$ represents a heterocyclic group having from 3 to 7 ring atoms, of which from 1 to 3 are nitrogen, oxygen or sulphur atoms, the remainder being carbon atoms. At least one of the ring atoms should be a carbon atom. Where there are 3 hetero-atoms, it is preferred that at least one is a nitrogen atom. Examples of such groups include the 2- and 3-furoyl, 2- and 3-thenoyl, 2-pyridinecarbonyl, nicotinoyl, isonicotinoyl, prolyl, piperidinecarbonyl, piperazinecarbonyl and morpholinocarbonyl groups.

Where $R^1$ and/or $R^2$ represents a residue of an amino acid, this may be any amino acid in which a hydroxy group has been removed from the or a carboxy (—COOH) group. Examples of such amino acid residues include the alanyl, β-alanyl, cystathionyl, cystyl, glycyl, histidyl, homoseryl, isoleucyl, lanthionyl, leucyl, lysyl, methionyl, norleucyl, norvalyl, omithyl, prolyl, sarcosyl, seryl, threonyl, thyronyl, tyrosyl, valyl, cysteinyl, homocysteinyl, tryptophyl, α-aspartyl, β-aspartyl, aspartoyl, asparaginyl, α-glutamyl, γ-glutamyl, and glutaminyl groups.

Where $R^c$ represents an alkanoyl group, this may be a straight or branched chain group having from 1 to 6 carbon atoms, and examples include the formyl, acetyl, propionyl, butyryl, isobutyryl, valeryl, isovaleryl, pivaloyl, hexanoyl, and heptanoyl groups, of which those groups having from 2 to 5 carbon atoms are preferred, the acetyl and propionyl groups being more preferred, and the acetyl group being most preferred.

Where substituent $\psi$ or substituent $\xi$ is an alkylamino group having from 1 to 6 carbon atoms, the alkyl part may be any of the alkyl groups defined and exemplified above. Preferred examples of such alkylamino groups include the methylamino, ethylamino, propylamino, isopropylamino, butylamino, isobutylamino, sec-butylamino, t-butylamino, pentylamino, isopentylamino, neopentylamino, t-pentylamino, hexylamino, and isohexylamino groups, of which those groups having from 1 to 4 carbon atoms are preferred, the methylamino and ethylamino groups being most preferred.

Where substituent $\psi$ or substituent $\xi$ is a dialkylamino group, each alkyl part has from 1 to 6 carbon atoms, and the two alkyl groups may be the same as or different from each other. The alkyl groups may be any of the alkyl groups defined and exemplified above. Preferred examples of such dialkylamino groups include the dimethylamino, methylethylamino, diethylamino, methylpropylamino, dipropylamino, diisopropylamino, ethylbutylamino, dibutylamino, di-t-butylamino, methylpentylamino, dipentylamino, diisopentylamino, and dihexylamino groups, of which those groups having from 1 to 4 carbon atoms in each alkyl group are preferred, the dimethylamino and diethylamino groups being most preferred.

Where substituent $\psi$ or substituent $\xi$ is an alkoxy group, this may be a straight or branched chain alkoxy group having from 1 to 6 carbon atoms, and examples include the methoxy, ethoxy, propoxy, isopropoxy, butoxy, isobutoxy, sec-butoxy, t-butoxy, pentyloxy, isopentyloxy, neopentyloxy, t-pentyloxy, hexyloxy, and isohexyloxy groups, of which those groups having from 1 to 4 carbon atoms are preferred, the methoxy and ethoxy groups being most preferred.

Where substituent ψ or substituent ξ is an alkylthio group having from 1 to 6 carbon atoms, the alkyl part may be any of the alkyl groups defined and exemplified above. Preferred examples of such alkylthio groups include the methylthio, ethylthio, propylthio, isopropylthio, butylthio, isobutylthio, sec-butylthio, t-butylthio, pentylthio, isopentylthio, neopentylthio, t-pentylthio, hexylthio, and isohexylthio groups, of which those groups having from 1 to 4 carbon atoms are preferred, the methylthio and ethylthio groups being most preferred.

Where substituent ψ or substituent ξ is an alkoxycarbonyl group, this may be a straight or branched chain alkoxycarbonyl group having from 2 to 7 carbon atoms, and examples include the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, neopentyloxycarbonyl, t-pentyloxycarbonyl, hexyloxycarbonyl, and isohexyloxycarbonyl groups, of which those groups having from 1 to 4 carbon atoms are preferred, the methoxycarbonyl and ethoxycarbonyl groups being most preferred.

Where substituent ξ is a hydroxyalkyl group having from 1 to 6 carbon atoms, the alkyl part may be any of the alkyl groups defined and exemplified above. Preferred examples of such hydroxyalkyl groups include the hydroxymethyl, 1- and 2-hydroxyethyl, 1-, 2- and 3-hydroxypropyl, 1,2-dihydroxyethyl, 1,2,3-trihydroxy-propyl, 4-hydroxybutyl, 5-hydroxypentyl and 6-hydroxyhexyl groups.

Where substituent ξ is a haloalkyl group having from 1 to 6, preferably from 1 to 4, carbon atoms, the alkyl part may be as defined and exemplified above, and the halogen atom is preferably chlorine, fluorine, bromine or iodine. Examples of such groups include the fluoromethyl, chloromethyl, bromomethyl, iodomethyl, dichloromethyl, difluoromethyl, trichloromethyl, trifluoromethyl, 2,2,2-trichloroethyl, 2-chloroethyl, 2-fluoroethyl, 2-bromoethyl, 2-iodoethyl, 2,2-dibromoethyl, 2,2,2-tribromoethyl, 3-fluoropropyl, 3-chloropropyl, 4-bromobutyl, 4-fluorobutyl, 5-fluoropentyl and 6-fluorohexyl groups.

It will be appreciated that, where the compound contains a group of formula —OR, where R is any of the groups and atoms defined above in relation to $R^1$ etc., the active species is likely to be the compound containing the free hydroxy group. Accordingly, any group that can be converted in vivo to a hydroxy group may be used in place of the hydroxy group.

Specific examples of compounds which may be used in the present invention include:

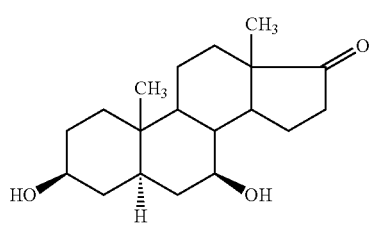

7β-hydroxy-epiandrosterone
(7β-hydroxy-EPIA)

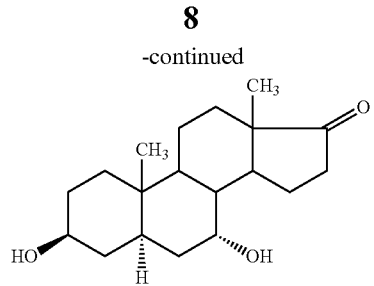

7α-hydroxy-epiandrosterone
(7α-hydroxy-EPIA)

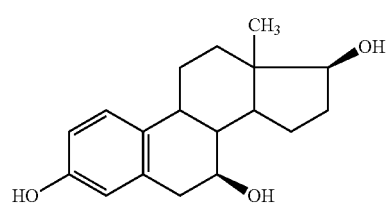

7β-hydroxy-17β-oestradiol

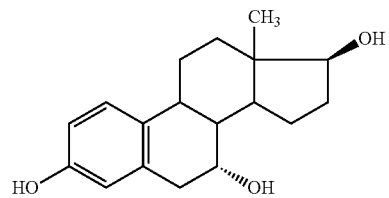

7α-hydroxy-17β-oestradiol

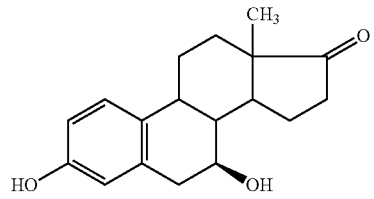

7β-hydroxy-oestrone

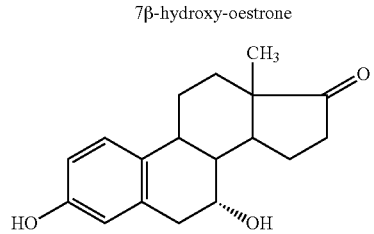

7α-hydroxy-oestrone

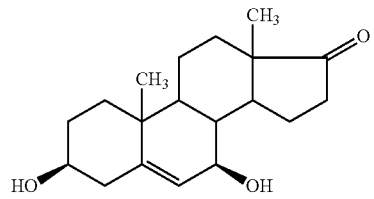

7β-hydroxy-dehydroepiandrosterone
(7β-hydroxy-DHEA)

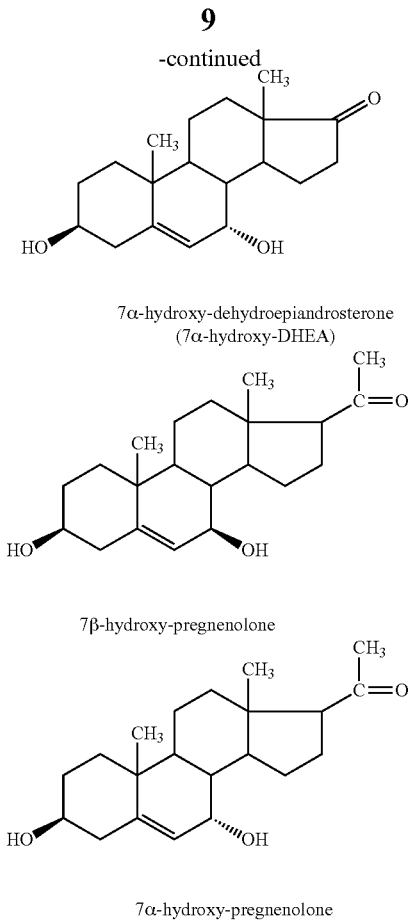

7α-hydroxy-dehydroepiandrosterone
(7α-hydroxy-DHEA)

7β-hydroxy-pregnenolone

7α-hydroxy-pregnenolone

Of the compounds listed above, the 7β-isomers are preferred.

Where the compounds of the present invention contain a hydroxy group, they may be converted to corresponding salts or esters, as is well known in the art, and there is no particular limitation upon the nature of the salt or ester produced. Where these salts or esters are to be administered to a patient, then they should be pharmaceutically acceptable. However, if the compound is intended for some other purpose, e.g. as an intermediate in another synthesis, then even this restriction is not necessary. Salts and esters may be chosen from those well known in the art for this type of compound. Preferred esters are the carboxylic esters and the amino acid esters, such as, for example, the alanine, O-alanine, cystathionine, cystine, glycine, histidine, homoserine, isoleucine, lanthionine, leucine, lysine, methionine, norleucine, norvaline, ornithine, proline, sarcosine, serine, threonine, thyronine, tyrosine, valine, cysteine, homocysteine, tryptophan, aspartic acid, asparagine, glutamic acid, and glutamine.

The compounds of the present invention may be prepared by a variety of processes, well known in themselves, starting from the parent steroids. For example, they may be prepared by the methods described in the literature referred to above, which would give a mixture of the 7β and corresponding 7α compounds, which may then, if desired, be separated by well known techniques. However, in some circumstances it may be desired or convenient to use the mixture of 7α and 7β isomers without separating them.

As an example, 7α-hydroxy EPIA and 7β-hydroxy EPIA may be obtained from DHEA by allylic oxidation after protection of the 3β-hydroxy group and the 17-ketone group using conventional methods. The product is then reduced with a soluble metal compound catalyst (such as sodium hydride) and the 3β-hydroxy and 17-ketone groups are deprotected. The 7α-hydroxy and 7β-hydroxy epimers may then be separated by conventional means, for example column chromatography, and the 7α-hydroxy EPIA and 7β-hydroxy EPIA may be crystallised to purity.

An alternative synthetic method is shown in the following reaction scheme:

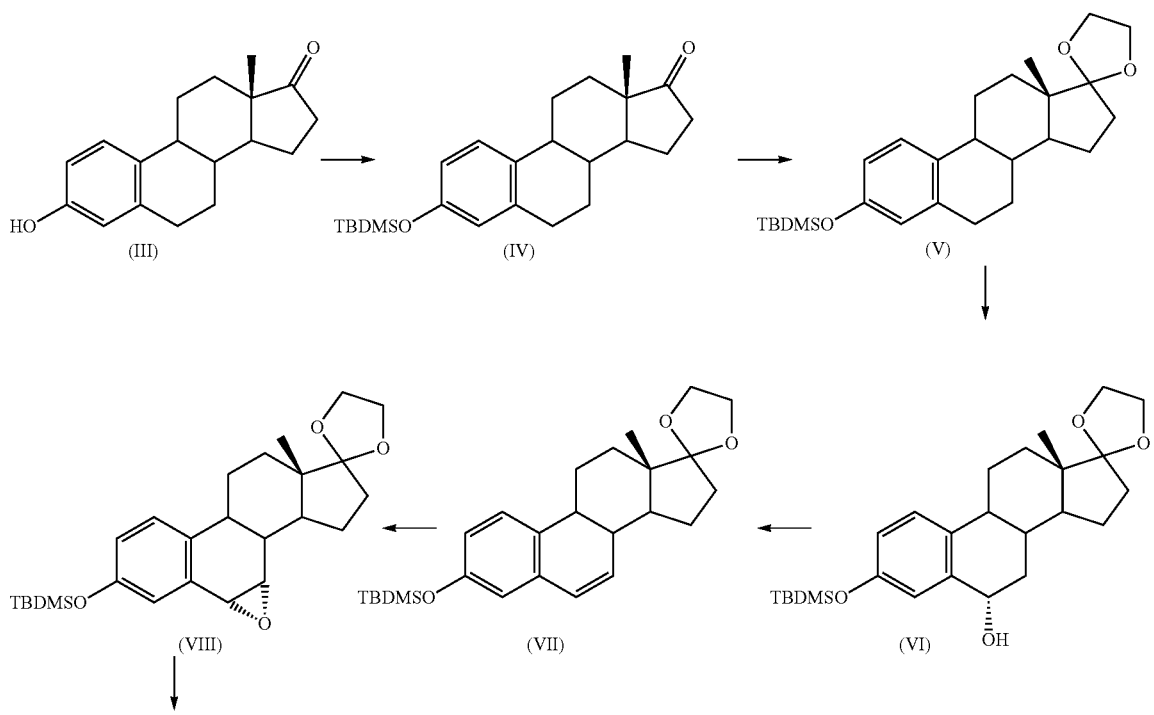

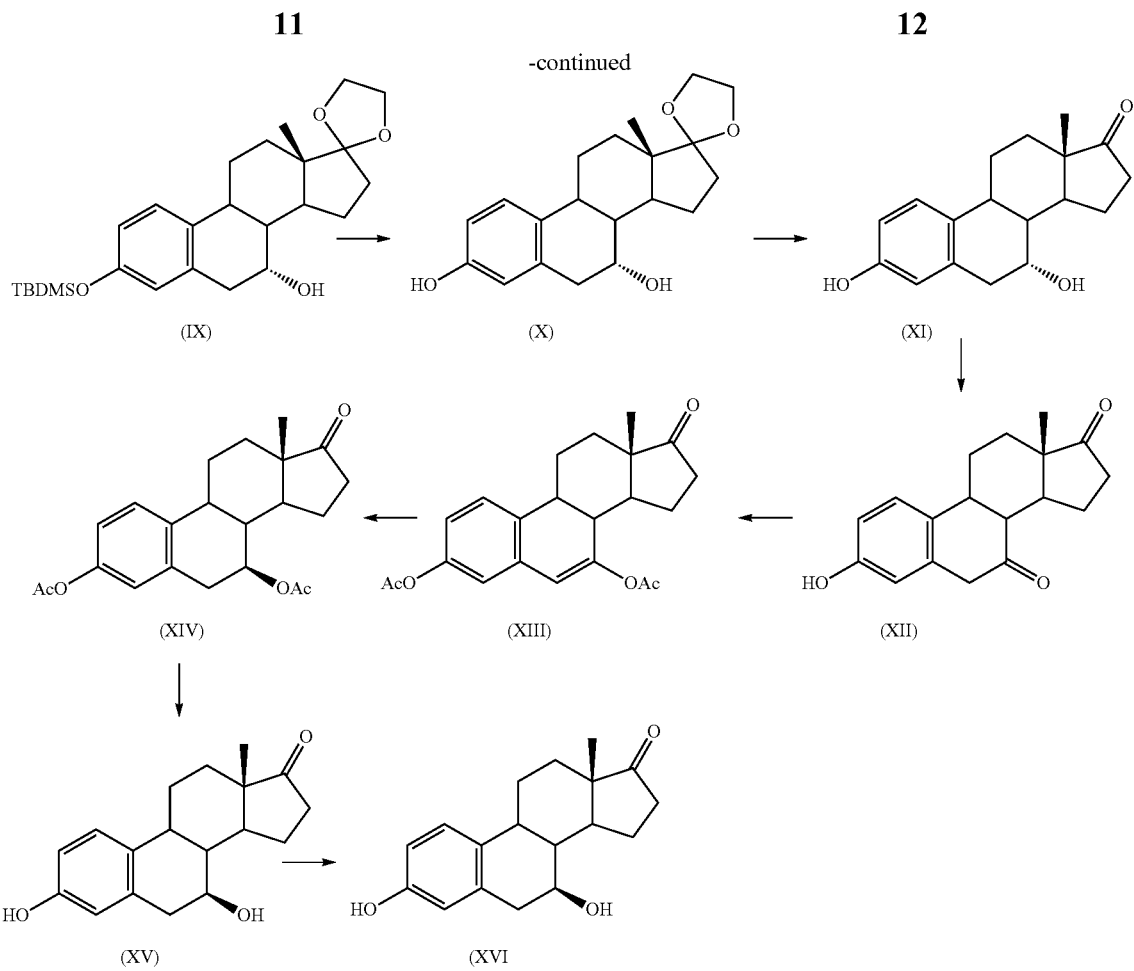

In the above formulae, TBDMSO represents t-butyldimethylsilyloxy and Ac represents acetyl. These abbreviations have the same meanings when used hereafter.

In the first step of the above reaction scheme, the compound of formula (III), oestrone, is protected by a t-butyldimethylsilyloxy group in a conventional manner to give the protected compound of formula (IV). This is then reacted with ethylene glycol in the presence of an acid catalyst (such as p-toluenesulphonic acid) to protect the keto group at the 17 position and give the compound of formula (V). A hydroxy group may then be introduced at the 6-position as illustrated hereafter in Example 3, to give the compound of formula (VI), which is then dehydrated to give the compound of formula (VII). This is epoxidised to give the compound of formula (VIII), which is then reduced to the compound of formula (IX), with a 7α-hydroxy group. The t-butyldimethylsilyl protecting group is removed, giving the compound of formula (X), and this is heated with a catalytic amount of an acid, to give 7α-hydroxy-oestrone (XI), which may be used in the present invention. This may then be oxidised, e.g. using chromic acid/sulphuric acid, to give the 7-keto-oestrone (XII), which is then reacted with acetic anhydride, to give the compound of formula (XIII). This compound is hydrogenated, e.g. using hydrogen in the presence of a palladium catalyst, to give the compound of formula (XIV), and finally the acetyl groups are removed, to give 7β-hydroxy-oestrone (XV), a compound of the present invention. If desired, this may be reduced, to give 7β-hydroxy-oestradiol (XVI), also a compound of the present invention. The corresponding 7α compound may be prepared in an analogous manner from 7α-hydroxy-oestrone (XI).

Other 7α- and 7β-hydroxy-compounds of the present invention may be prepared in a similar manner, for example, 7β-hydroxy-DHEA may be prepared as illustrated by the following reaction scheme:

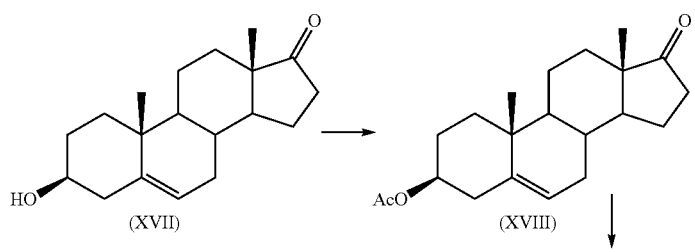

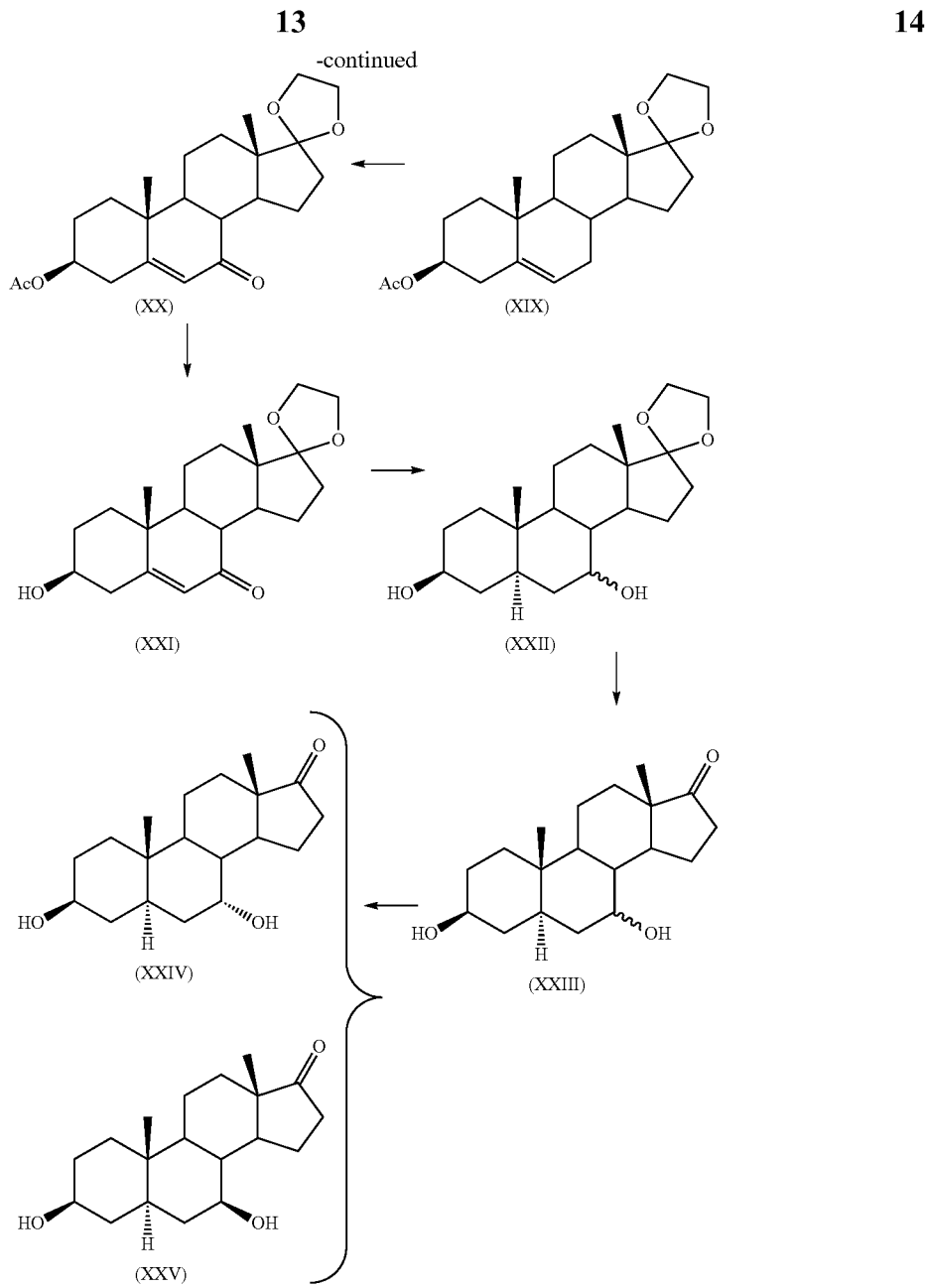

In this reaction scheme, DHEA (XVII) is acetylated to give the corresponding acetate of formula (XVIII), which is then reacted with ethylene glycol, to give the ketal of formula (XIX). The ketal (XIX) is then oxidised as described in Example 16, to give the corresponding 7-keto compound (XX), which is then deacetylated, to give the compound of formula (XXI). This is reduced, to give 7-hydroxy-17-ketal-EPIA of formula (XXII), which is then treated with an acid to remove the ketal group and give 7-hydroxy-EPIA, which is finally separated into the 7β- and 7α-isomers by chromatography, to give 7α-hydroxy-EPIA (XXIV) and 7β-hydroxy-EPIA (XXV).

Each of the steps of the above reaction schemes is individually well known and may be carried out using known solvents and catalysts (if appropriate) and under known reaction conditions, for example conditions of time and temperature.

The compounds defined above have a neuroprotective effect. In accordance with the present invention, we have found that they also have a cardioprotective effect, and so can be used for the prevention or treatment of cardiac diseases arising from ischaemic damage, for example myocardial infarction. They also have the ability to protect against ischaemic renal damage, for example glomerulonephritis or acute renal damage. In general, based on the activity demonstrated, it is predictable that they will have a similar protective effect on tissues of other peripheral organs.

Indeed, the compounds of the present invention can also be used to treat spinal cord injury.

The compounds of the present invention may be applied to the patient if it is suspected that they are in danger of an ischaemic event, especially a myocardial infarction or ischaemic renal damage. Such prophylactic application may be exceedingly useful. However, it has also been demonstrated that the compounds of the present invention have useful activity, even if applied after an ischaemic event, but it will be appreciated that it is preferred to administer the compounds as soon as possible, in order to avoid as much myocardial or renal tissue damage as possible. In some circumstances it may be desirable to administer repeated doses, especially where the patient remains in danger of an ischaemic event.

The compounds may also be administered prophylactically in anticipation of a spinal cord injury or may be used to treat such an injury after it has occurred.

Suitable methods of administration are generally by injection, in order to achieve the desired result as soon as possible. Thus, intravenous injection is particularly preferred.

The dose of the compound of the present invention will vary depending upon many factors, including the age, body weight and general condition of the patient, as well as the mode, frequency and route of administration. However, a dose of from 0.01 to 50 mg/kg body weight is generally recommended, a dose of from 0.05 to 20 mg/kg body weight being more preferred. This may be administered in a single dose or in divided doses.

The invention is further illustrated by the following non-limiting Examples, of which Examples 1 to 20 illustrate the preparation of compounds of the present invention and Examples 21 to 23 illustrate their activity. In Examples 1 to 20, the Roman numerals refer to the formulae in the reaction schemes shown above.

EXAMPLE 1

3-t-Butyldimethylsilyl-oestrone (IV)

4.25 g of t-butyldimethylsilyl chloride (28.2 mmol, 3 eq.) were added to a solution of 50 ml of dimethylformamide (DMF) containing 2.54 g of oestrone (III) (9.41 mmol, 1 eq.) and 3.84 g of imidazole (56.5 mmol, 6 eq.) in a 100 ml three-necked flask. The mixture was then left overnight at room temperature under a nitrogen atmosphere. A 10% w/v aqueous potassium carbonate solution was added to the reaction medium, which was then extracted with ethyl acetate. The organic phase was washed with water and then dried over anhydrous sodium sulphate and evaporated to dryness. 3.76 g of 3-t-butyldimethylsilyl-oestrone (IV) (9.41 mmol, 100%) were obtained.

EXAMPLE 2

17-Ketal-3-t-butyldimethylsilyl-oestrone (V)

A solution of 60 ml of toluene containing 3 g of 3-t-butyldimethylsilyl-oestrone (IV) (7.50 mmol), 3 ml of ethylene glycol and a catalytic amount of p-toluenesulphonic acid was heated to reflux with steam distillation using a Dean-Stark apparatus for 24 hours. The reaction medium was then poured into 50 ml of a 10% w/v aqueous potassium carbonate solution. The organic phase was decanted. The aqueous phase was extracted with ethyl acetate. The organic phases were combined and evaporated to dryness. 3.16 g of 17-ketal-3-t-butyldimethylsilyl-oestrone (V) (7.12 mmol, 95%) were obtained.

EXAMPLE 3

6α-Hydroxy-17-ketal-3-t-butyldimethylsilyl-oestrone (VI)

In a 1 liter three-necked flask, a solution of 100 ml of anhydrous tetrahydrofuran (THF) was degassed by nitrogen flushing and cooled to −80° C. Diisopropylamine (20 ml, 143.30 mmol) was added to the reaction medium. A 15% w/v butyllithium solution in cyclohexane (89.9 ml, 143.30 mmol) was added dropwise to the reaction medium. After 10 minutes, a solution of 100 ml of anhydrous THF, previously degassed, containing 17.5 g of potassium t-butyrate was added dropwise to the reaction medium. After a further 15 minutes, a solution of 50 ml of anhydrous THF, previously degassed, containing 12.27 g of 17-ketal-3-t-butyldimethylsilyl-oestrone (V) (27.63 mmol) was added dropwise to the reaction medium. The reaction mixture was left for 2 hours at −80° C. At the end of this time, 48 ml of trimethyl borate (429.90 mmol) were added dropwise at −80° C. to the reaction medium, which was left at 0° C. for 1 hour. 100 ml of 30% v/v aqueous hydrogen peroxide solution were then added. The reaction mixture was left for 1 hour at room temperature and then 500 ml of water were added. The reaction medium was extracted with ethyl acetate. The organic phase was washed with a 10% w/v aqueous sodium thiosulphate solution, washed with water, dried over anhydrous sodium sulphate and evaporated to dryness. The residue was purified by flash chromatography (SiO2/ethyl acetate:cyclohexane 1/9 then 2/8). 6.35 g of 6α-hydroxy-17-ketal-3-t-butyldimethylsilyl-oestrone (VI) (13.81 mmol, 50%) were obtained.

EXAMPLE 4

17-Ketal-3-t-butyldimethylsilyl-6-dehydroestrone (VII)

A solution of 40 ml of toluene containing 1.54 g of 6α-hydroxy-17-ketal-3-t-butyldimethylsilyl-oestrone (VI) (3.35 mmol), 4 ml of ethylene glycol and a catalytic amount of p-toluenesulphonic acid was heated to reflux with steam distillation using a Dean-Stark apparatus for 24 hours. The reaction medium was then poured into 50 ml of a 10% w/v aqueous potassium carbonate solution. The organic phase was decanted. The aqueous phase was then extracted with ethyl acetate. The organic phases were combined and evaporated to dryness. 1.48 g of 17-ketal-3-t-butyldimethylsilyl-6-dehydroestrone (VII) (3.35 mmol, 100%) were obtained.

EXAMPLE 5

17-Ketal-3-t-butyldimethylsilyl-6α,7α-epoxy-oestrone (VIII)

A solution of 20 ml of dichloromethane containing 1.16 g of m-chlorobenzoic acid (55%, 3.69 mmol, 1.1 eq.) was added dropwise, at 0° C., to a solution of 20 ml of dichloromethane containing 1.85 g of 17-ketal-3-t-butyldimethylsilyl-6-dehydroestrone (VII) (3.36 mmol, 1 eq.). The reaction medium was poured, after 2 hours, into a 10% w/v aqueous sodium hydrogen carbonate solution and then extracted with ethyl acetate. The organic phase was dried over anhydrous sodium sulphate and then evaporated to dryness. The residue was purified by flash chromatography (SiO2/ethyl acetate:cyclohexane 1/9). 769 mg of 17-ketal-3-t-butyldimethylsilyl-6α,7α-epoxyoestrone (VIII) (1.68 mmol, 50%) were obtained.

EXAMPLE 6

7α-Hydroxy-17-ketal-3-t-butyldimethylsilyl-oestrone (IX)

200 mg of lithium aluminium hydride (5.40 mmol, 2 eq.) were added to a solution of 50 ml of anhydrous THF containing 1.13 g of 17-ketal-3-t-butyldimethylsilyl-6α,7α-epoxy-oestrone (VIII) (2.60 mmol, 1 eq.). The reaction medium was heated to reflux for 2 hours and then cooled, poured into ice, filtered through a Celite (trade mark) filter aid and extracted with ethyl acetate. The organic phase was dried over anhydrous sodium sulphate and then evaporated to dryness. The residue was purified by flash chromatography (SiO2/ethyl acetate:cyclohexane 1/9). 837 mg of 7α-hydroxy-17-ketal-3-t-butyldimethylsilyl-oestrone (IX) (1.82 mmol, 70%) were obtained.

EXAMPLE 7

7α-Hydroxy-17-ketal-oestrone (X)

A solution of 20 ml of THF containing 1.5 g of tetrabutylammonium chloride (4.78 mmol, 1.10 eq.) was added, at room temperature, to a solution of 50 ml of THF containing 2 g of 7α-hydroxy-17-ketal-3-t-butyldimethylsilyl-oestrone (IX) (4.35 mmol, 1 eq.). The reaction medium was poured into 70 ml of a 10% w/v aqueous sodium carbonate solution. The reaction medium was extracted with ethyl acetate. The organic phase was dried over anhydrous sodium sulphate and then evaporated to dryness. 1.39 g of 7α-hydroxy-17-ketal-oestrone (X) (4.22 mmol, 97%) were obtained.

EXAMPLE 8

7α-Hydroxy-oestrone (XI)

A solution of 50 ml of acetone containing 1 ml of water, 1.0 g of 7α-hydroxy-17-ketal-oestrone (X) (3.03 mmol) and a catalytic amount of p-toluenesulphonic acid was heated to reflux for 2 hours. The reaction medium was then poured into 70 ml of a 10% w/v aqueous sodium carbonate solution. The reaction medium was extracted with ethyl acetate. The organic phase was dried over anhydrous sodium sulphate and then evaporated to dryness. 814 mg of 7α-hydroxy-oestrone (XI), (2.85 mmol, 94%), which was recrystallised from ethyl acetate, were obtained.

EXAMPLE 9

7-Ketoestrone (XII)

An 8 N solution of chromic acid in sulphuric acid was added dropwise, until the yellow colour persisted, to a solution cooled to 0° C. of 40 ml of acetone containing 300 mg of 7α-hydroxy-oestrone (XI) (1.05 mmol). The reaction medium was poured into 50 ml of water and then extracted with ethyl acetate. The organic phase was washed with an aqueous sodium carbonate solution and then dried over anhydrous sodium sulphate and evaporated to dryness. The residue was purified by flash chromatography (SiO2/ethyl acetate: cyclohexane 3/7). 200 mg of 7-keto-estrone (XII) (0.70 mmol, 67%) were obtained.

EXAMPLE 10

7-Hydroxy-6-dehydroestrone3,7-diacetate (XIII)

A solution of 10 ml of acetic anhydride containing 5 g of anhydrous sodium acetate and 1 g of 7-keto-oestrone (XII) (3.52 mmol) was heated to reflux for 1 hour. The reaction medium was then cooled and then poured into water and extracted with diethyl ether. The organic phase was washed with an aqueous sodium carbonate solution and then dried over anhydrous sodium sulphate and evaporated to dryness. The residue was purified by flash chromatography (SiO2/ethyl acetate): cyclohexane 1/9). 1.25 g of 7-hydroxy-6-dehydroestrone-3,7-diacetate (XIII) (3.41 mmol, 97%) were obtained.

EXAMPLE 11

7-Hydroxyestrone 3,7-diacetate (XIV)

A solution of 80 ml of glacial acetic acid containing 1.0 g of 7-hydroxy-6-dehydroestrone-3,7-diacetate (XIII) (2.72 mmol) was hydrogenated with 200 mg of 10% palladium on charcoal catalyst under a hydrogen pressure of 1 bar. The reaction medium was filtered after 2 hours and evaporated to dryness. The residue was purified by flash chromatography (SiO2/ethyl acetate:cyclohexane 1/9). 855 mg of 7-hydroxyestrone3,7-diacetate (XIV) (2.31 mmol, 85%) were obtained.

EXAMPLE 12

7β-Hydroxyoestrone (XV)

A solution of 50 ml of methanol containing 1% of potassium hydroxide and 1 g of 7-hydroxyestrone-3,7-diacetate (XIV) (2.70 mmol) was heated to reflux for 2 hours. The reaction medium was then cooled, neutralised and then extracted with ethyl acetate. The organic phase was dried over anhydrous sodium sulphate and then evaporated to dryness. 695 mg of 7β-hydroxyoestrone (XV) (2.43 mmol, 90%), which was recrystallised from methanol, were obtained.

EXAMPLE 13

7β-Hydroxyoestradiol (XVI)

264 mg of sodium borohydride (7.00 mmol, 2 eq.) were added to a solution of 50 ml of methanol containing 1.0 g of 7β-hydroxyoestrone IXV) (3.50 mmol). The reaction medium was poured into water and extracted with ethyl acetate. The organic phase was dried over anhydrous sodium sulphate and then evaporated to dryness. 917 mg of 7β-hydroxyoestradiol (XVI) (3.18 mmol, 91%), which was recrystallised from methanol, were obtained.

EXAMPLE 14

DHEA-3-acetate (XVIII)

A solution of 50 ml of pyridine and 50 ml of acetic anhydride containing 10 g of DHEA (XVII) (34.72 mmol) was heated to reflux for 4 hours. The reaction medium was cooled, poured into water and extracted with ethyl acetate. The organic phase was dried over anhydrous sodium sulphate and evaporated to dryness. 11.0 g of DHEA-3-acetate (XVIII) (33.33 mmol, 96%), which was recrystallised from ethanol, were obtained.

EXAMPLE 15

17-Ketal-DHEA-3-acetate (XIX)

A solution of 100 ml of toluene containing 5 g of DHEA-3-acetate (15.15 mmol), 5 ml of ethylene glycol and a catalytic amount of p-toluenesulphonic acid was heated to reflux with steam distillation using a Dean-Stark apparatus for 24 hours. The reaction medium was poured into 100 ml of a 10% w/v aqueous potassium carbonate solution. The organic phase was decanted. The aqueous phase was extracted with ethyl acetate. The organic phases were combined and evaporated to dryness. 5.10 g of 17-ketal-3-DHEA-acetate (XIX) (13.64 mmol, 90%), which was recrystallised from ethanol, were obtained.

EXAMPLE 16

7-Keto-17-ketal-DHEA-3-acetate (XX)

A solution of 70 ml of pyridine containing 5 g of 17-ketal-DHEA-3-acetate (XIX) (13.37 mmol) and a catalytic amount of Bengal Rose was irradiated using a medium-pressure mercury vapour lamp with oxygen sparging. A catalytic amount of copper acetate was added to the reaction medium after 24 hours. The reaction medium, after 24 hours, was evaporated to dryness. The residue was purified by flash chromatography (SiO2/ethyl acetate:cyclohexane 3/7). 3.11 g of 7-keto-17-ketal-DHEA-3-acetate (XX) (8.02 mmol, 60%) were obtained.

EXAMPLE 17

7-Keto-17-ketal-DHEA (XXI)

A solution of 50 ml of methanol containing 1% of potassium hydroxide and 1 g of 7-keto-17-ketal-DHEA-3-acetate (XX) (2.58 mmol) was heated to reflux for 2 hours. The reaction medium was then cooled, neutralised and then extracted with ethyl acetate. The organic phase was dried over anhydrous sodium sulphate and then evaporated to dryness. 802 mg of 7-keto-17-ketal-DHEA (XXI) (2.32 mmol, 90%), which was recrystallised from methanol, were obtained.

EXAMPLE 18

7-Hydroxy-17-ketal-EPIA (XXII)

10 g of 7-keto-17-ketal-DHEA (XXI) (28.90 mmol) were added to a liquid ammonia solution at −33° C. containing 2.65 g of sodium. After 4 hours, ammonium chloride was added until the blue colour disappeared. 2.65 g of sodium were then added. After 4 hours, ammonium chloride was again added until the blue colour disappeared. Water was added and the ammonia was allowed to evaporate. The reaction medium was extracted with ethyl acetate. The organic phase was dried over anhydrous sodium sulphate and then evaporated to dryness. 6.07 g of 7-hydroxy-17-ketal-EPIA (XXII) (17.34 mmol, 60%) were obtained.

EXAMPLE 19

7-Hydroxy-EPIA (XXIII)

A solution of 100 ml of acetone containing 5 ml of water, 10 g of 7-hydroxy-17-ketal-EPIA (XXII) (28.57 mmol, 50%) and a catalytic amount of paratoluenesulphonic acid was heated to reflux for 4 hours. The reaction medium was cooled, poured into 100 ml of a 10% w/v aqueous sodium carbonate solution and then extracted with ethyl acetate. The organic phase was dried over anhydrous sodium sulphate and then evaporated to dryness. The residue was purified by flash chromatography (SiO$_2$/ethyl acetate). 5.24 g of 7-hydroxy-EPIA (XXIII) (17.14 mmol, 60%) were obtained.

EXAMPLE 20

7α-Hydroxy-EPIA (XXIV) & 7β-hydroxy-EPIA (XXV)

7-Hydroxy-EPIA (XXIII) (5 g) containing 7α and 7β epimers in a ratio 65/35 was purified by flash chromatography (Al$_2$O$_3$/CHCl$_3$). 7β-Hydroxy-EPIA (XXV) (2.5 g) was obtained first, before 7α-hydroxy-EPIA (XXIV) (1.34 g). 7β-Hydroxy-EPIA (XXV) and 7α-hydroxy-EPIA (XXIV) were recrystallised from ethyl acetate.

EXAMPLE 21

Protocol For Studying Hypoxic Neuronal Damage

Organotypic hippocampal slice cultures were prepared using the basic method of Pringle et al (1996, 1997) modified as follows:

Wistar rat pups (8-11 days old) were decapitated and the hippocampus rapidly dissected into ice-cold Gey's balanced salt solution supplemented with 4.5 mg/ml glucose. Slices were separated and plated onto Millicell CM culture inserts (4 per well) and maintained at 37° C./5% CO$_2$ for 14 days. Maintenance medium consisted of 25% heat-inactivated horse serum, 25% Hank's balanced salt solution (HBSS) and 50% minimum essential medium with added Earle's salts (MEM) supplemented with 1 mM glutamine and 4.5 mg/ml glucose. Medium was changed every 3-4 days.

Experimental hypoxia was performed as described previously (Pringle et al., 1996; 1997). Briefly, cultures were transferred to serum free medium (SFM-75% MEM, 25% HBSS supplemented with 1 mM glutamine and 4.5 mg/ml glucose) containing 5 µg/ml of the fluorescent exclusion dye propidium iodide (PI). Cultures were allowed to equilibrate in SFM for 60 minutes prior to imaging. PI fluorescence was detected using a Leica inverted microscope fitted with a rhodamine filter set. Any cultures in which PI fluorescence was detected at this stage were excluded from further study. Hypoxia was induced by transferring cultures to SFM (+PI) which had been saturated with 95% N$_2$/5% CO$_2$. Culture plates (without lids) were then sealed into an airtight chamber in which the atmosphere was saturated with 95% N$_2$/5% CO$_2$ by continuously blowing through gas at 10 liters/minute for ten minutes before being sealed and placed in the incubator for 170 minutes (total time of hypoxia was therefore 180 minutes). At the end of the hypoxic period cultures were returned to normoxic SFM containing PI and placed back in the incubator for 24 hours.

Neuronal damage was assessed as described previously (Pringle et al., 1996; 1997) using either NIH Image 1.60 running on an Apple IIsi computer or OpenLab 2.1 (Improvision) running on a Macintosh G4/400. Images were captured using a monochrome camera and saved onto optical disk for offline analysis. Light transmission images were captured prior to the addition of drugs, and PI fluorescence images recorded at the end of the 24-hour post-hypoxia recovery period. The area of the CA1 cell layer was determined from the transmission image. The area of PI fluorescence in CA1 was measured using the density slice function within NIH Image or OpenLab, and neuronal damage expressed as the percentage of the CA1 in which PI fluorescence was detected above background.

Steroid compounds were prepared by making an initial 1 mg/ml solution in ethanol and further diluting down in SFM. Compounds were added to the cultures for 45 minutes prior to hypoxia, during the hypoxic episode and during the posthypoxic recovery period. Control experiments consisted of cultures treated with vehicle alone.

Results

Experiment 1

An initial experiment was performed to determine whether 7αOH-EPIA and 7βOH-EPIA were neuroprotective at a high concentration of 100 nM. Hypoxia produced a lesion in 25.5±6.4% of CA1. This damage was significantly reduced by both 7αOH-EPIA and 7βOH-EPIA when present pre-, during and post-hypoxia (see Table I).

TABLE I

| Compound | N | % Damage in CA1 |
|---|---|---|
| Control Hypoxia | 17 | 25.5 ± 6.4 |
| Hypoxia + 100 nM 7αOH-EPIA | 16 | 4.0 ± 2.9** |
| Hypoxia +100 nM 7βOH-EPIA | 16 | 9.0 ± 4.7* |

Experiment 2

Having determined that both the α- and β-isomers of 7OH-EPIA were neuroprotective, we assessed the concentration-dependency of this effect. Control hypoxia resulted in neuronal damage to 31.9±4.7% of the CA1. 7βOH-EPIA was significantly neuroprotective at 10 nM and 100 nM, but activity was lost if the concentration was reduced to 1 nM. as shown in Table II, below.

TABLE II

| Compound | N | % Damage in CA1 |
|---|---|---|
| Control Hypoxia | 29 | 31.9 ± 4.7 |
| Hypoxia + 1 nM 7βOH-EPIA | 15 | 20.6 ± 7.2 |
| Hypoxia + 10 nM 7βOH-EPIA | 12 | 11.9 ± 4.7* |
| Hypoxia + 100 nM 7βOH-EPIA | 13 | 14.3 ± 5.0* |

Experiment 3

Having observed the neuroprotective activity of 7βOH-EPIA, we next investigated whether 7βOH-DHEA was neuroprotective. Cultures were incubated with either 100 nM 7βOH-DHEA or vehicle, pre-, during and post-hypoxia. Hypoxia produced damage in 29.0±6.2% of CA1. In cultures treated with 7βOH-DHEA, a large, highly significant, reduction in neuronal damage was observed as shown in Table III, below.

TABLE III

| Compound | N | % Damage in CA1 |
|---|---|---|
| Control Hypoxia | 21 | 29.0 ± 6.2 |
| Hypoxia + 100 nM 7βOH-DHEA | 16 | 4.1 ± 1.9** |

EXAMPLE 22

Global Cerebral Ischaemia in Rats

4 Vessel Occlusion

Cerebral ischaemia was induced by four-vessel-occlusion (4VO) in male Wistar rats (250-280 g). Both vertebral arteries were occluded by electrocauterization in pentobarbital anaesthesia (60 mg/kg i.p.). The animals were allowed to recover for 24 hours with free access to water but not food. The next day the carotid arteries were exposed under 2% halothane in 30% oxygen/70% nitrous oxide anaesthesia and were occluded for 10 minutes using microvascular clamps. Subsequently, both clamps were removed and both arteries were inspected for immediate reperfusion. During the operation and the following 3 hours normothermia of the animals (37.5±0.5° C.) was maintained by using a thermostatically controlled heating blanket connected to a rectal thermometer. For control, in sham-operated animals both vertebral arteries were cauterised in pentobarbital anaesthesia and both common carotid arteries were exposed but not clamped under 2% halothane in 30% oxygen/70% nitrous oxide anaesthesia the following day. The wound was treated with lidocaine gel and then sutured. The animals were kept under a heating lamp at 30° C. environmental temperature until they regained consciousness.

Seven groups of animals were investigated:
1. (n=8) steroid compound, 7β-OH EPIA (0.1 mg/kg, i.v. via tail vein, three injections: 15 minutes prior to the induction of ischaemia, during ischaemia and 5 minutes after reperfusion);
2. (n=8) steroid compound, 7β-OH EPIA (0.3 mg/kg, i.v. three injections as described in 1.);
3. (n=8) steroid compound, 7β-OH EPIA (1 mg/kg, i.v., three injections as described in 1.);
4. (n=8) NBQX (disodium salt, because more water soluble) as reference substance and positive control (TOCRIS, Germany, 30 mg/kg, i.p., three injections as described in 1.);
5. (n=8) received vehicle (0.9% NaCl, containing 100 μl Ethanol) three injections as described in 1.);
6. (n=8) ischaemia alone;
7. (n=8) sham operated controls.

NBQX was 2,3-dihydroxy-6-nitro-7-sulfamoyl-benzo(F) quinoxaline and was known to have neuroprotective activity [Gill, R., Nordholm, L., Lodge D.: The neuroprotective action of 2,3-dihydroxy-6-nitro-7-sulfamoyl-benzo(F)quinoxaline (NBQX) in a rat focal ischaemia model. Brain Res. 580, 35-43, 1992].

7β-OH EPIA was 7β-hydroxyepiandrosterone, a compound of the present invention.

The substances were dissolved in 100 μl ethanol and finally diluted with 0.9% NaCl.

After a survival time of 7 days after ischaemia, all animals were perfusion fixed tanscardially with 4% paraformaldehyde. The brains were then removed carefully and postfixed in the same fixative for 2 hours. After cryoprotection in 30% sucrose, the brains were rapidly frozen in isopentane and stored at −80° C. Twenty-micrometer cryostat sections comprising the hippocampal formation were Nissl stained with toluidine blue or NeuroTrace fluorescence.

Data Analysis:

The severity of neuronal damage in the hippocampal CA1 region after ischaemia was evaluated by the number of surviving neurons using Nissl staining. The mean number of morphologically intact neurons per 400 μm length was calculated in CA1 region for each group. Cell counting was performed in 3-5 serial sections per animal and 6 times 400 μm CA1 area per section using a light microscope equipped with a 20× objective. The data were statistically analysed by paired Student's t-test. Data were presented as mean±SEM.

Results and Discussion

Morphological intact hippocampal CA1 neurons were characterised by Nissl staining (toluidine blue and NeuroTrace) with the following criteria: clear shape of a neuronal perikarya, large nucleus with a positive labelled nucleolus, a small cytoplasm zone around the nucleus with positive Nissl staining, indicating the intact rough endoplasmic reticulum with ribosomes and therefore the intact protein synthesis machinery.

Figure 1A:
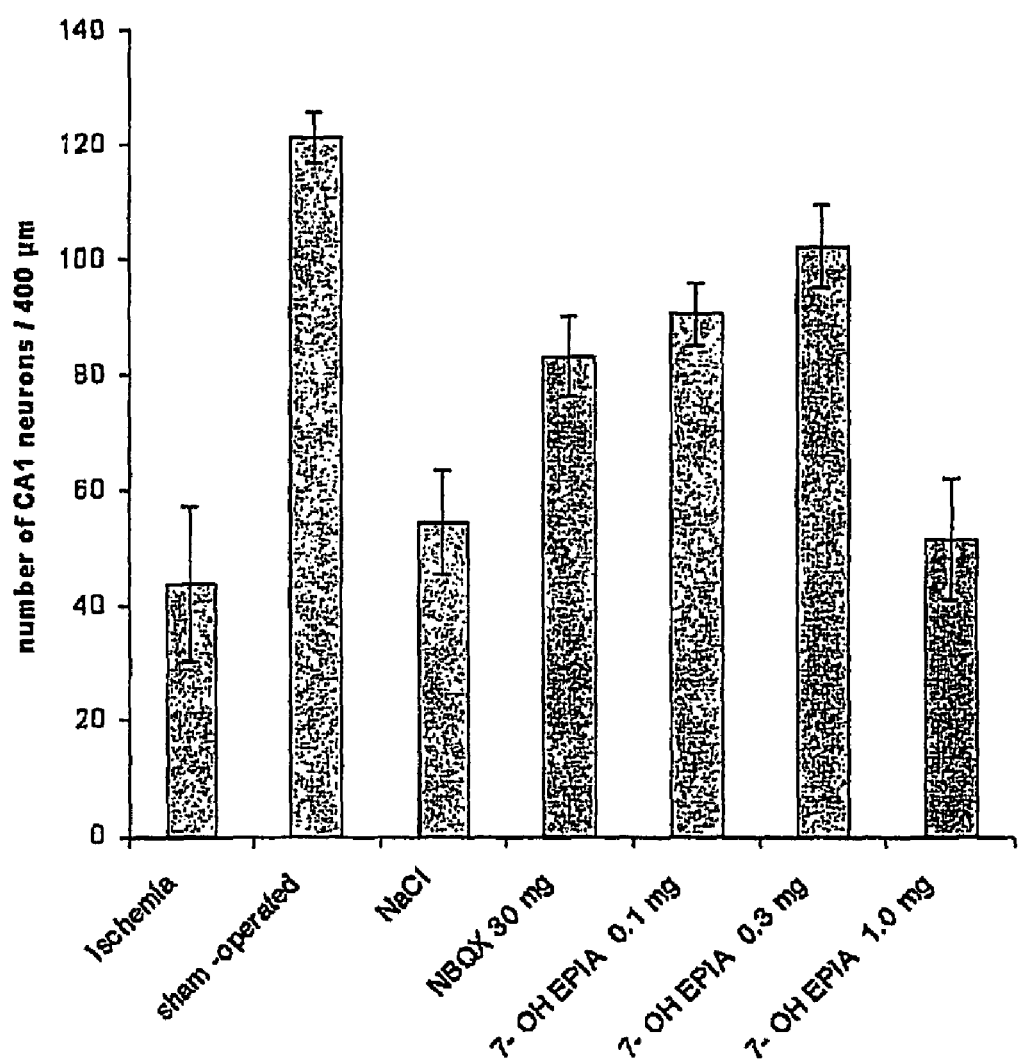
FIG. 1A shows data relating to Example 22 presented as mean number±SEM of intact neurons per 400 μm length of CA1 region.
Figure 1B:
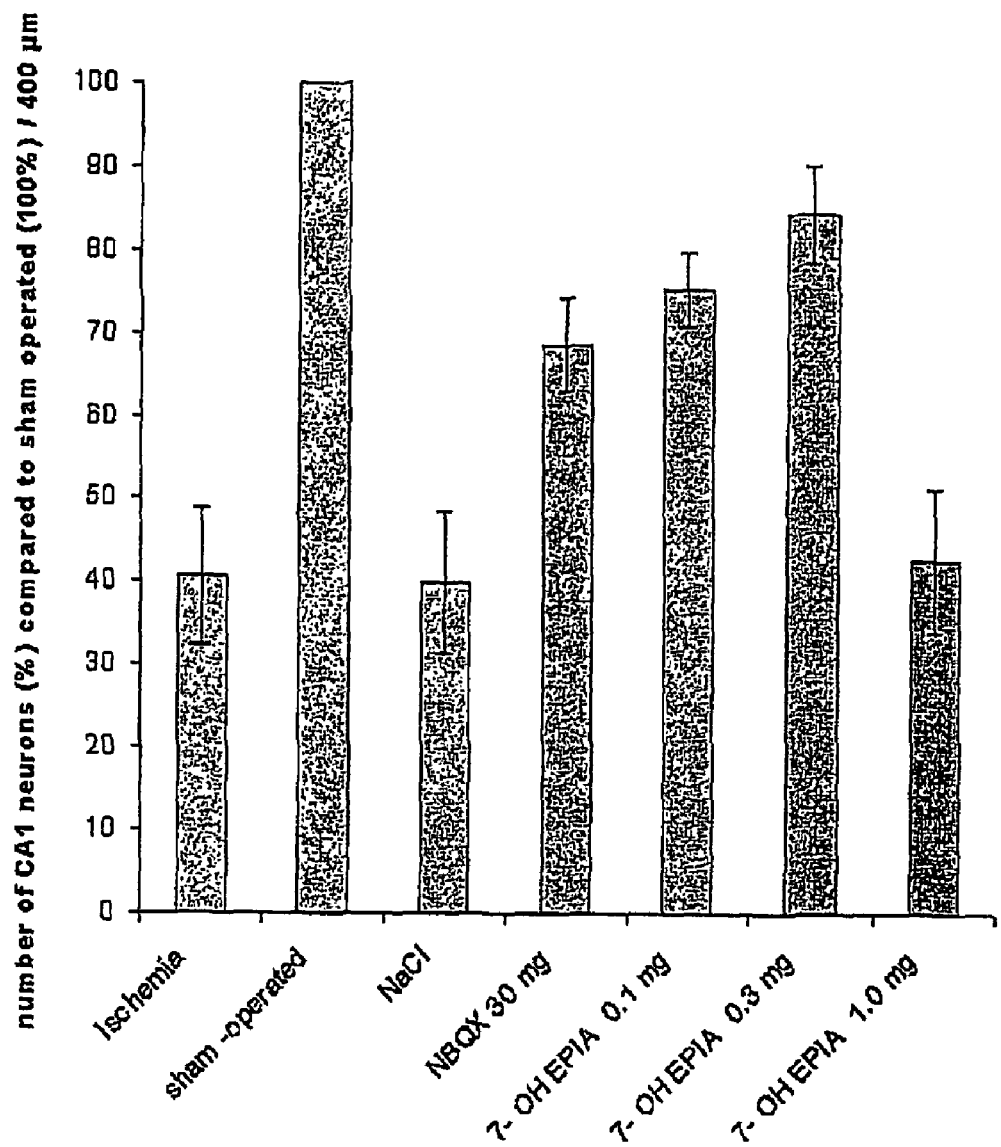
FIG. 1B shows data of Example 22 expressed as percentage of intact neurons per 400 μm length of CA1 region compared to sham operated animals set as 100%.
Figure 2:
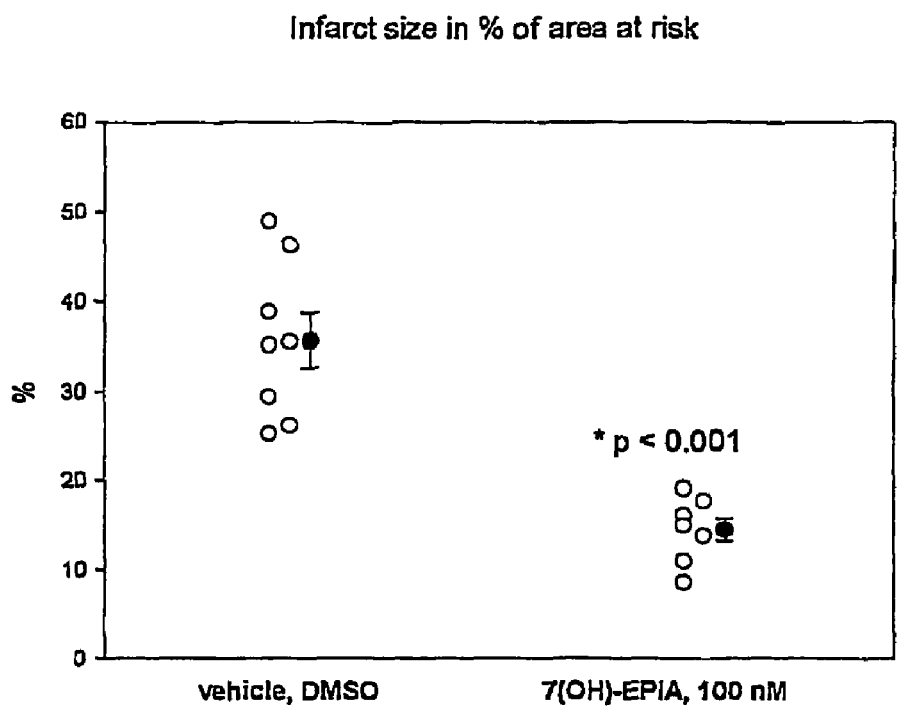
FIG. 2 shows infarct size in Example 23 in control vehicle treated hearts and 7β-OH EPIA treated hearts before, during and after regional ischaemia; 7β-OH EPIA was added to the perfusate at 25 minutes, regional ischaemia was introduced at 55 minutes, the ischaemic area was reperfused at 85 minutes.
Figure 3:
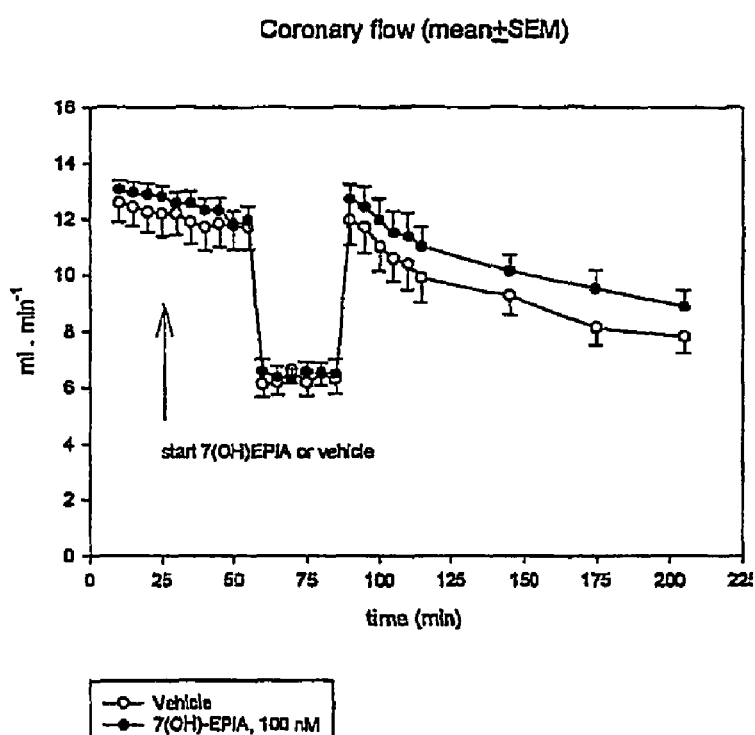
FIG. 3 shows coronary flow in Example 23 in control vehicle treated hearts and 7β-OH EPIA treated hearts before, during and after regional ischaemia; 7β-OH EPIA was added to the perfusate at 25 minutes, regional ischaemia was introduced at 55 minutes, the ischaemic area was reperfused at 85 minutes.
Figure 4:
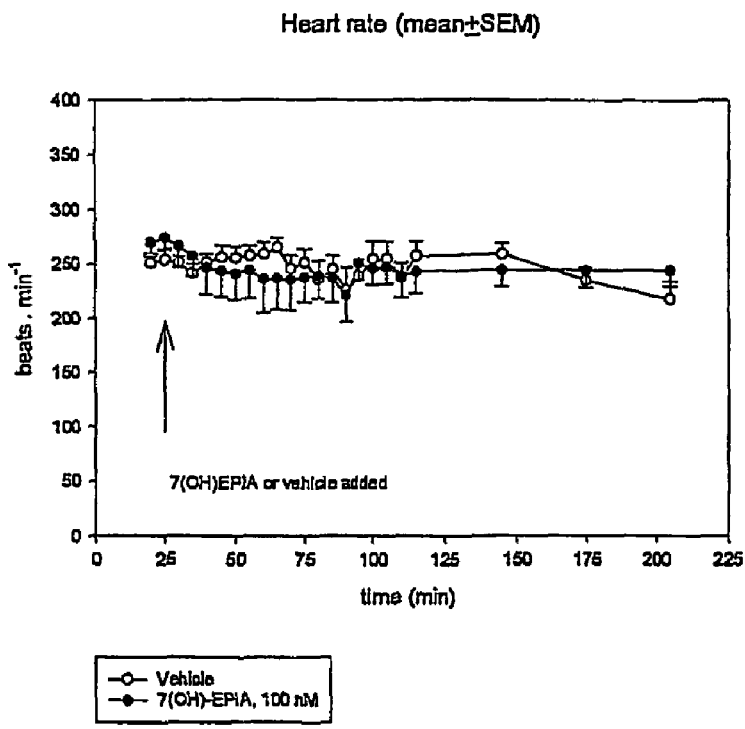
FIG. 4 shows heart rate in Example 23 in control vehicle treated hearts and 7β-OH EPIA treated hearts before, during and after regional ischaemia; 7β-OH EPIA was added to the perfusate at 25 minutes, regional ischaemia was introduced at 55 minutes, the ischaemic area was reperfused at 85 minutes.

10 minutes of global ischaemia (mild ischaemia) and a survival time of 7 days leads to a neurodegeneration of pyramidal cells selectively in the hippocampal CA1 region (FIGS. 1A-1C). The mean number of pyramidal cells in CA1 of sham operated animals was 121.5±4.3 (set as 100%). Therefore, 60% of CA1 neurons died after 10 minutes of global ischaemia (FIG. 1B). The number of neurons in the animal group of ischaemia and i.v. injection of vehicle (NaCl plus 100 µl Ethanol) applied as described in the experiment was comparable to that of the ischaemia group alone (FIG. 1A, 1B). NBQX (30 mg/kg, iv., three injections as described in the experiment) showed a significant (p=0.03) neuroprotection in CA1 pyramidal cells compared to the ischaemia group. Compared to the ischaemia alone NBQX leads to a 47.5% neuroprotection while compared to the sham operated animals the protective effect was 68.5%. The neuroprotection caused by NBQX was in agreement with Gill et al., 1992 and Gill 1994 demonstrating the validity of the global ischaemia model we used in our experiments. 7β-OH EPIA leads to a concentration dependent neuroprotection of hippocampal CA1 pyramidal cells after 10 minutes of global ischaemia and a survival time of 7 days (FIG. 1A). T-test analysis revealed a highly significant neuroprotective effect of 7β-OH EPIA in concentrations of 0.1 mg/kg (p=0.01) and 0.3 mg/kg (p=0.0008). Compared to the sham operated group 7β-OH EPIA showed a 74.8% (0.1 mg/kg) and a 83.9% (0.3 mg/kg) neuroprotective effect on CA1 pyramidal cells, respectively (FIG. 1C). 7β-OH EPIA in a concentration of 1.0 mg/kg showed only a tendency to neuroprotection, but the effect was not significant.

In all experiments with 7β-OH EPIA injected i.v. prior, during and after ischaemia we never observed any behavioural abnormalities of the animals.

LEGENDS OF THE FIGURES

Number of morphological intact hippocampal CA1 pyramidal cells in rats 7 days after global cerebral ischaemia in rats and under the influence of different compounds.

FIG. 1A: Data were presented as mean number±SEM of intact neurons per 400 µm length of CA1 region.

FIG. 1B: Data were expressed as percentage of intact neurons per 400 µm length of CA1 region compared to sham operated animals set as 100%.

FIG. 1C: Data were presented as absolute percentage of neuroprotection when the number of surviving neurons in the ischaemia group was set to zero and those of the sham operated group was set to 100%.

Although the above data demonstrate neuroprotection, it has recently been shown that Cyp7b1, the enzyme responsible for 7-hydroxylation of 3-hydroxy steroids and which thus results in the conversion of oestradiol, DHEA and EPIA to their neuroprotective derivatives, is present in other tissues subject to ischaemic injury, including cardiac and renal tissues. Accordingly, it can be deduced from the above data that the compounds of the present invention would protect cardiac and renal tissues from ischaemic injury.

EXAMPLE 23

Cardioprotective Effect

The study was designed to test the potential anti-ischaemic and cardioprotective effect of 7β-OH EPIA in Langendorf perfused male rat hearts. The end point for evaluation of protection in this model is infarct size (protection against lethal injury, cell death). The infarct size model used is based on a standardised ischaemic insult followed by reperfusion. In the current study, treatment was added ex vivo (to the perfusion solution of the isolated heart) for 30 minutes prior to infarction and continued through 30 minutes regional ischaemia (infarction) and 120 minutes of reperfusion. Based on results from pilot studies, a concentration of 100 nM was used and compared to vehicle treated hearts. The drug was dissolved in DMSO (vehicle) and the final concentration of DMSO in the perfusion solution was $1:10^{-6}$. The results of the study showed that the compound at a concentration of 100 nM reduced infarct size significantly from 46.3+/−2.49 to 14.4+/−1.22% of the ischaemic risk zone (p<0.001). Heart function in conjunction with drug addition was also examined, and addition of 7β-OH EPIA by itself did not result in detectable changes in heart function. Hearts treated with 7β-OH EPIA showed a slight reduction in global left ventricular systolic pressure parameters during regional ischaemia (p<0.05 at 25 minutes regional ischaemia), which disappeared after reperfusion.

The study confirms cardioprotective, anti-ischaemic properties of the compound at a concentration of 100 nM in the isolated perfused, male rat heart.

Animal Treatment

Animals were housed in the animal department of the University of Tromsø and treated according to the guidelines formulated by the European Convention for the protection of vertebrate animals used for experimental or other purposes. Supply of Wistar rats were from Harland (The Netherlands), and the rats stayed in the animal department for one week before experiments were started. Animal weight was restricted to 240-380 g, and only male hearts were used. This corresponds to age 60-120 days. On the day of the experiment, rats were transferred in a filter cabinet from the animal department to the laboratory. The rats were then anaesthetised by pentobarbital injection intraperitoneally (50-75 mg/kg) and heparinized by 200 IU also intraperitoneally.

Perfusion

The hearts were rapidly (within 1-2 minutes) transferred to a perfusion set up using Krebs Henseleits bicarbonate buffer as the perfusion solution. Perfusate and heart were maintained at 37° C.

The Krebs Henseleits bicarbonate buffer consisted of:

| | |
|---|---|
| NaCl | 118.5 mM/liter |
| NaHCO$_3$ | 25.0 mM/liter |
| KCl | 4.7 mM/liter |
| KH$_2$PO$_4$ | 1.2 mM/liter |
| MgSO$_4$ | 1.2 mM/liter |
| CaCl$_2$ | 2.4 mM/liter |
| glucose | 11.1 mM/liter |

The buffer was equilibrated with a gas mixture of approximately 5% CO$_2$ in O$_2$.

The perfusion pressure was 100 mm H$_2$O. A latex balloon was mounted on the tip of polyvinyl tubing, connected to a pressure transducer and inserted into the cavity of the left ventricle for measurements of left ventricular pressure. The size of the balloon was not changed during the experiment and the experimental set up was therefore an isovolumetric left ventricle preparation. Timed collections of venous effluate from the right side of the heart (sinus coronarius via the pulmonary trunk and the right atrium) were used for coronary flow measurements. Heart rate was calculated from pressure recordings.

Computer-based data acquisition and analysis were used for heart function (Lab View based software).

Experimental Protocol

The stabilisation period was 20-25 minutes, and hearts which did not reach a stable performance during this period, were discharged. Hearts with a LVDP (left ventricular developed pressure) between 80 mmHg and 175 mmHg, diastolic pressure between 0-10 mmHg and coronary flow between 9 to 18 ml/min at the end of the stabilisation period were used.

A 100 mM stock solution of 7β-OH EPIA in DMSO was made and stored as aliquots in eppendorf tubes at 20° C. This solution was further diluted in perfusion solution to 100 nM of active drug just prior to the experiment. Pretreatments with 7β-OH EPIA (n=8) or vehicle (n=8) were given for 30 minutes before infarction and continued until the end of experiments.

Regional ischaemia (infarction) was achieved by placing a silk suture around the main branch of the left coronary artery. Reversible ligation was obtained by using a small piece of a polyvinyl tube. The standardised regional ischaemia lasted 30 minutes, and hearts were then reperfused for 2 hours.

Infarct Size and Risk Zone Size

At the end of the experiment the following procedure was followed:

1) The left coronary artery was re-ligated
2) A suspension of blue dye was added to the perfusion line. The ischaemic zone was identified as the area without dye.
3) The heart was quickly removed, weighed and frozen.
4) One day thereafter the heart was cut in 2 mm thick slices and stained with tetrazolium. The heart slices were incubated for 20 minutes in 1% TTC (triphenyl-tetrazolium-chloride) in 0.2 M phosphate buffer (pH 7.4) at 37° C. Infarcted tissue will not develop any colour reaction whereas surviving tissue develops a purple colour due to the presence of dehydrogenases and cofactors in the tissue.
5) After staining, hearts were placed in formalin (4%) for fixation.
6) TTC staining will be lost with time and all heart slices were therefore computer scanned and saved as digital images for documentation.
7) Computer based planimetry was used to calculate volume of the ventricles, the ischaemic risk zone and infarct. Results are presented as infarct in % of ischaemic risk zone.

Results

The results are shown in the following Table 1.

TABLE 1

Body weight, heart weight, left ventricle volume, risk zone volume and infarct volume (mean SEM) in the control and treated group.

|  | control (n = 8) | 7β-OH EPIA (n = 8) |
|---|---|---|
| Rat weight (g) | 295.6 +/− 5.30 | 285.6 +/− 7.93 |
| heart weight (g) | 1.3 +/− 0.04 | 1.3 +/− 0.04 |
| ventricle volume (mm3) | 239.0 +/− 17.73 | 200.3 +/− 9.23 |
| Risk zone volume (mm3) | 109.3 +/− 8.43 | 98.9 +/− 6.51 |
| Infarct volume | 38.9 +/− 4.98 | 14.1 +/− 1.46 * p < 0.001 |
| Risk zone/ventricle (%) | 35.7 +/− 3.11 | 49.3 +/− 2.38 |
| Infarct/risk zone (%) | 46.3 +/− 2.49 | 14.4 +/− 1.22 * p < 0.001 |

The results are also illustrated in FIGS. 2 to 6 of the accompanying drawings.

Infarct:

There was a significant difference between the two groups ($p<0.001$) with a marked infarct reduction in the drug treated group. Infarcts in the control vehicle treated hearts were comparable in size to the standard control infarcts usually obtained in untreated hearts subjected to 30 minutes regional ischaemia.

Heart Function:

Heart function was examined throughout the experimental time course. A marked decrease in coronary flow was seen in conjunction with the coronary artery occlusion in this experimental model and confirms that the intended coronary occlusion took place. Coronary flow was not influenced by the addition of 7β-OH EPIA. Heart-rate was not significantly different between the two groups and remained stable throughout the experiment. Left ventricular developed pressure (LVDP) also declines during regional ischaemia. This decline was larger in drug treated hearts compared to the control. A significant difference in LVDP between the groups was seen at 25 minutes of regional ischaemia. No differences between the two groups were observed in diastolic pressure.

Vehicle:

Vehicle DMSO has previously been used as a vehicle in buffer-perfused hearts and the results indicate that under the circumstances of the current study this compound has no detectable influence by itself.

CONCLUSION

The study demonstrated a marked and significant cardioprotective effect of 7β-OH EPIA. The extent of protection is comparable in magnitude to some of the most potent and well characterised cardioprotective drugs or treatment regimes like NHE blockade or ischaemic preconditioning when used in the same experimental model.

The invention claimed is:

1. A method of protecting a mammal against ischaemia-induced tissue damage in peripheral organs, comprising administering to a patient in need thereof, wherein said patient is a mammal, an effective amount of a steroid in which the steroid is a compound of formula (I):

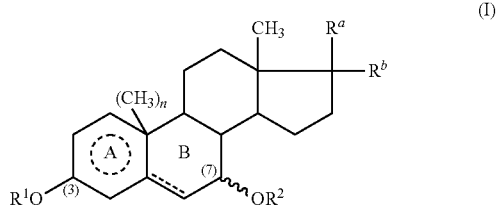

wherein
  $R^1$ and $R^2$ represent a hydrogen atom;
  the —$OR^2$ group at the 7-position is in the β-configuration;
  one of $R^a$ and $R^b$ represents a group of formula —$R^c$ in the β configuration, and the other represents a hydrogen atom, or $R^a$ and $R^b$ together represent an oxo group;
  $R^c$ represents an aryl-carbonyl group, in which the aryl part is an aromatic carbocyclic group having from 6 to 10 ring carbon atoms, a heterocyclic-carbonyl group, as defined below, or a group of formula —$OR^4$, where $R^4$ represents a hydrogen atom, an alkyl group having from 1 to 6 carbon atoms, an alkenyl group having from 2 to 6 carbon atoms, an alkynyl group having from 2 to 6 carbon atoms, an aryl group having from 6 to 10 carbon atoms, a formyl group, an alkylcarbonyl group having from 2 to 7 carbon atoms, an alkenylcarbonyl group having from 3 to 7 carbon atoms, an alkynylcarbonyl group having from 3 to 7 carbon atoms, an arylcarbonyl group having from 7 to 11 carbon atoms, an aralkylcarbonyl group having from 8 to 15 carbon atoms, an aralkenylcarbonyl group having from 9 to 15 carbon atoms, a residue of an amino acid, or a heterocyclic-carbonyl group, as defined herein;

the ring A,

is a benzene or cyclohexane ring;

when ring A is a cyclohexane ring, the dotted line in ring B represents a single carbon-carbon bond and n is 1; or when ring A is a benzene ring, the dotted line in ring B represents a single carbon-carbon bond and n is 0;

said heterocyclic-carbonyl group is a group of formula $R^3$—CO, where $R^3$ represents a heterocyclic group having from 3 to 7 ring atoms, of which from 1 to 3 are hetero-atoms selected from nitrogen atoms, oxygen atoms and sulphur atoms, and the remaining atom or atoms of which there is at least one is or are carbon atoms;

said alkyl, alkenyl and alkynyl groups and the alkyl, alkenyl and alkynyl parts of said alkylcarbonyl, alkenylcarbonyl and alkynylcarbonyl groups being unsubstituted or having at least one of the following substituents $\psi$:

substituents $\psi$: hydroxy groups, mercapto groups, halogen atoms, amino groups, alkylamino groups having from 1 to 6 carbon atoms, dialkylamino groups in which each alkyl group has from 1 to 6 carbon atoms, carbamoyl groups, nitro groups, alkoxy groups having from 1 to 6 carbon atoms, alkylthio groups having from 1 to 6 carbon atoms, carboxy groups, alkoxycarbonyl groups and unsubstituted aryl groups having from 6 to 10 carbon atoms;

said aryl groups, said heterocyclic groups, and the aryl parts of said arylcarbonyl groups and said aralkylcarbonyl groups being unsubstituted or having at least one of the following substituents $\xi$:

substituents $\xi$: any of substituents $\psi$, and alkyl groups having from 1 to 6 carbon atoms, hydroxyalkyl groups having from 1 to 6 carbon atoms, and haloalkyl groups having from 1 to 6 carbon atoms;

and pharmaceutically acceptable salts and esters thereof.

2. The method according to claim 1, in which:

one of $R^a$ and $R^b$ represents group of formula —$OR^4$, where $R^4$ represents a hydrogen atom, an alkyl group having from 1 to 6 carbon atoms, an alkenyl group having from 2 to 6 carbon atoms, an alkynyl group having from 2 to 6 carbon atoms, an aryl group having from 6 to 10 carbon atoms, a formyl group, an alkylcarbonyl group having from 2 to 7 carbon atoms, an alkenylcarbonyl group having from 3 to 7 carbon atoms, an alkynylcarbonyl group having from 3 to 7 carbon atoms, an arylcarbonyl group having from 7 to 11 carbon atoms, an aralkylcarbonyl group having from 8 to 15 carbon atoms, an aralkenylcarbonyl group having from 9 to 15 carbon atoms, a residue of an amino acid, or a heterocyclic-carbonyl group, in the β configuration, and the other represents a hydrogen atom, or $R^a$ and $R^b$ together represent an oxo group;

said heterocyclic-carbonyl group is a group of formula $R^3$—CO, where $R^3$ represents a heterocyclic group having from 3 to 7 ring atoms, of which from 1 to 3 are hetero-atoms selected from nitrogen atoms, oxygen atoms and sulphur atoms, and the remaining atom or atoms of which there is at least one is or are carbon atoms.

3. The method according to claim 1, in which the steroid is 7β-hydroxy-epiandrosterone.

4. The method according to any one of claims 1, 2, and 3, in which the peripheral organ is the heart.

5. The method according to claim 4, in which the damage to the heart is caused by a myocardial infarction.

* * * * *